(12) United States Patent
Patterson et al.

(10) Patent No.: US 6,759,008 B1
(45) Date of Patent: *Jul. 6, 2004

(54) APPARATUS AND METHOD FOR BLOOD OXYGENATION

(75) Inventors: William R. Patterson, Irvine, CA (US); Jeffrey L. Creech, Los Angeles, CA (US)

(73) Assignee: Therox, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/410,179

(22) Filed: Sep. 30, 1999

(51) Int. Cl.⁷ .......................... A61M 1/36; A61M 37/00
(52) U.S. Cl. .......................... 422/45; 422/44; 604/4.01; 604/6.14; 604/6.16
(58) Field of Search .................. 422/44–48; 604/4.01, 604/5.01, 6.01, 6.09, 6.11, 6.12, 6.14, 6.16, 264, 523–25, 529, 533–35; 261/75, 76, 115, DIG. 28, DIG. 27, 78.1–78.2; 435/1.1, 1.2, 283.1, 284.1, 286.6–286.7, 297.1–297.2, 297.4, 818; 128/898, 200.18–200.23, 220.14, DIG. 3; 210/758–61

(56) References Cited

U.S. PATENT DOCUMENTS

| | | | |
|---|---|---|---|
| 2,474,665 A | 6/1949 | Guarino | 128/214 |
| 3,142,296 A | 7/1964 | Love | 128/214 |

(List continued on next page.)

FOREIGN PATENT DOCUMENTS

| | | | |
|---|---|---|---|
| DE | 2 343 845 | 3/1974 | |
| DE | 2649126 A1 | 5/1978 | B01F/3/04 |
| GB | 1506555 | 4/1978 | A61M/1/03 |
| WO | WO 92/14404 | 9/1992 | A61B/6/00 |
| WO | WO 92/14976 | 9/1992 | F25B/19/00 |
| WO | WO 95/13843 | 5/1995 | A61M/37/00 |
| WO | WO 96/01593 | 1/1996 | A61B/19/00 |
| WO | WO 96/17565 | 6/1996 | A61F/5/00 |
| WO | WO 96/40334 | 12/1996 | A61M/15/00 |
| WO | WO 96/41987 | 12/1996 | |
| WO | WO 97/19713 | 6/1997 | |
| WO | WO 97/49447 | 12/1997 | A61M/25/00 |
| WO | WO 98/16203 | 4/1998 | A61K/9/133 |
| WO | WO 98/46340 | 10/1998 | |
| WO | WO 99/08732 | 2/1999 | A61M/1/32 |
| WO | WO 99/08733 | 2/1999 | A61M/1/36 |

OTHER PUBLICATIONS

U.S. patent application Ser. No. 08/581,019 filed Jan. 3, 1996, Spears "Stabilized Gas–Enriched and Gas–Supersaturated Liquids".

U.S. patent application Ser. No. 08/915/5332 filed Aug. 15, 1997, Spears et al., "Method of Generalized Extracorporeal Support".

(List continued on next page.)

*Primary Examiner*—Patricia M. Bianco
(74) *Attorney, Agent, or Firm*—Margaret A. Kivinski

(57) ABSTRACT

An apparatus for blood oxygenation and delivery is provided. The apparatus advantageously comprises a liquid-to-liquid oxygenation assembly with a pressurizable chamber having inlets for a first gas-supersaturated fluid and a second fluid, such as blood. The inlets are advantageously positioned on the mixing chamber in such a way that the first fluid and the second fluid enter the mixing chamber normally to each other to promote mixing and liquid-to-liquid gas transfer. The apparatus also includes a delivery system coupled to the blood oxygenation assembly. The delivery system includes a generally tubular elongated member having a proximal end portion, a distal end portion, and a transition portion located between the proximal end portion and the distal end portion. The transitional portion is relatively flexible compared to the proximal end portion and is relatively stiff compared to the distal end portion. In another embodiment, the delivery system includes a generally tubular elongated member having a proximal end portion and a distal end portion with a plurality of holes.

21 Claims, 11 Drawing Sheets

U.S. PATENT DOCUMENTS

| | | | |
|---|---|---|---|
| 3,437,450 A | 4/1969 | Greenwood | 23/285.5 |
| 3,512,517 A | 5/1970 | Kadish et al. | 128/2 |
| 3,721,231 A | 3/1973 | Hubert | 128/2.05 R |
| 3,881,483 A | 5/1975 | Sausse | 128/214 R |
| 3,927,981 A | 12/1975 | Viannay et al. | 23/258.5 |
| 4,008,047 A | 2/1977 | Petersen | 23/258.5 M |
| 4,041,180 A | 8/1977 | Wilson | 426/11 |
| 4,122,858 A | 10/1978 | Schiff | 128/348 |
| 4,205,042 A | 5/1980 | Lobdell et al. | 422/47 |
| 4,239,729 A | 12/1980 | Hasegawa et al. | 422/48 |
| 4,297,318 A | 10/1981 | Raible | 422/46 |
| 4,317,731 A | 3/1982 | Roberts, Jr. et al. | 210/741 |
| 4,401,431 A | 8/1983 | Arp | 604/4 |
| 4,442,843 A | 4/1984 | Rasor et al. | 128/660 |
| 4,445,896 A | 5/1984 | Gianturco | 604/238 |
| 4,466,804 A | 8/1984 | Hino | 604/4 |
| 4,493,692 A | 1/1985 | Reed | 604/4 |
| 4,596,210 A | 6/1986 | Schmidtke | 123/1 A |
| 4,602,987 A | 7/1986 | Bonaventura et al. | 204/129 |
| 4,610,661 A | 9/1986 | Possis et al. | 604/52 |
| 4,657,756 A | 4/1987 | Rasor et al. | 424/9 |
| 4,664,680 A | 5/1987 | Weber | 55/48 |
| 4,666,668 A | 5/1987 | Lidorenko et al. | 422/48 |
| 4,681,119 A | 7/1987 | Rasor et al. | 128/660 |
| 4,686,085 A | 8/1987 | Osterholm | 422/45 |
| 4,735,750 A | 4/1988 | Damann | 261/29 |
| 4,769,241 A | 9/1988 | Heldebrant et al. | 424/161 |
| 4,804,358 A * | 2/1989 | Karcher et al. | 600/17 |
| 4,808,378 A | 2/1989 | Nakanishi et al. | 422/48 |
| 4,828,543 A | 5/1989 | Weiss et al. | 604/4 |
| 4,871,450 A | 10/1989 | Goodrich et al. | 210/151 |
| 4,874,509 A | 10/1989 | Bullock | 210/169 |
| 4,874,581 A | 10/1989 | Sutherland et al. | 422/46 |
| 4,917,667 A | 4/1990 | Jackson | 604/96 |
| 4,919,895 A | 4/1990 | Heldebrant et al. | 422/129 |
| 4,968,483 A | 11/1990 | Müller et al. | 422/45 |
| 4,973,558 A | 11/1990 | Wilson et al. | 435/240.242 |
| 5,006,352 A | 4/1991 | Zelenák née Zoltai et al. | 426/67 |
| 5,039,482 A | 8/1991 | Panzani et al. | 422/46 |
| 5,069,661 A * | 12/1991 | Trudell | 128/DIG. 3 |
| 5,084,011 A | 1/1992 | Grady | 604/24 |
| 5,086,620 A | 2/1992 | Spears | 62/51.1 |
| 5,110,548 A | 5/1992 | Montevecchi | 422/48 |
| 5,152,964 A | 10/1992 | Leonard | 422/48 |
| 5,158,533 A | 10/1992 | Strauss et al. | 604/4 |
| 5,158,540 A | 10/1992 | Wijay et al. | 604/43 |
| 5,180,364 A | 1/1993 | Ginsburg | 604/53 |
| 5,186,713 A | 2/1993 | Raible | 604/4 |
| 5,195,971 A | 3/1993 | Sirhan | 604/96 |
| 5,261,875 A | 11/1993 | Spears | 604/24 |
| 5,277,176 A | 1/1994 | Habashi et al. | 128/200.24 |
| 5,322,500 A | 6/1994 | Johnson et al. | 604/4 |
| 5,334,142 A | 8/1994 | Paradis | 604/53 |
| 5,356,388 A | 10/1994 | Sepetka et al. | 604/164 |
| 5,368,555 A | 11/1994 | Sussman et al. | 604/4 |
| 5,380,307 A | 1/1995 | Chee et al. | 604/264 |
| 5,382,407 A | 1/1995 | Leonard | 422/48 |
| 5,407,426 A | 4/1995 | Spears | 4/24 |
| 5,413,558 A | 5/1995 | Paradis | 604/101 |
| 5,569,180 A | 10/1996 | Spears | 604/24 |
| 5,573,505 A | 11/1996 | Johnson et al. | 604/56 |
| 5,591,399 A | 1/1997 | Goldman et al. | 422/44 |
| 5,599,296 A | 2/1997 | Spears | 604/26 |
| 5,670,094 A | 9/1997 | Sasaki et al. | 261/27 |
| 5,693,017 A | 12/1997 | Spears et al. | 604/132 |
| 5,695,717 A | 12/1997 | Polaschegg et al. | 422/48 |
| 5,709,654 A | 1/1998 | Klatz et al. | 604/24 |
| 5,725,492 A | 3/1998 | Igo et al. | 604/4 |
| 5,730,330 A | 3/1998 | Reading | 222/113 |
| 5,730,698 A | 3/1998 | Fischell et al. | 600/3 |
| 5,730,935 A | 3/1998 | Spears | 422/44 |
| 5,735,934 A | 4/1998 | Spears | 75/414 |
| 5,752,929 A | 5/1998 | Klatz et al. | 604/51 |
| 5,766,490 A | 6/1998 | Taylor et al. | 210/758 |
| 5,782,811 A * | 7/1998 | Samson et al. | 604/527 |
| 5,797,874 A | 8/1998 | Spears | 604/53 |
| 5,797,876 A | 8/1998 | Spears et al. | 604/95 |
| 5,814,004 A | 9/1998 | Tamari | 604/4 |
| 5,814,222 A | 9/1998 | Zelenák et al. | 210/615 |
| 5,834,519 A | 11/1998 | Spears | 514/938 |
| 5,843,307 A | 12/1998 | Faivre et al. | 210/192 |
| 5,849,191 A | 12/1998 | Agranonik et al. | 210/608 |
| 5,874,093 A | 2/1999 | Eliaz et al. | 424/401 |
| 5,879,282 A | 3/1999 | Fischell et al. | 600/3 |
| 5,885,467 A | 3/1999 | Zelenák et al. | 210/758 |
| 5,888,611 A | 3/1999 | Leonard | 428/113 |
| 5,893,838 A | 4/1999 | Daoud et al. | 604/26 |
| 5,922,305 A | 7/1999 | Spears | 424/43 |
| 5,957,899 A | 9/1999 | Spears et al. | 604/264 |
| 5,958,377 A | 9/1999 | Spears | 424/43 |
| 5,976,119 A | 11/1999 | Spears et al. | 604/508 |
| 6,030,357 A | 2/2000 | Daoud et al. | 604/26 |
| 6,123,698 A | 9/2000 | Spears et al. | 604/523 |
| 6,142,971 A | 11/2000 | Daoud et al. | 604/23 |
| 6,169,117 B1 | 1/2001 | Spears | 514/37 |
| 6,180,059 B1 | 1/2001 | Divino, Jr. et al. | 422/45 |
| 6,197,279 B1 | 3/2001 | Spears | 424/43 |
| 6,235,007 B1 | 5/2001 | Divino, Jr. et al. | 604/264 |
| 6,238,645 B1 | 5/2001 | Spears | 424/43 |
| 6,248,087 B1 * | 6/2001 | Spears et al. | 604/6.14 |
| 6,387,324 B1 * | 5/2002 | Patterson et al. | 422/45 |
| 6,415,993 B1 * | 7/2002 | Forbert et al. | 239/434 |
| 6,454,997 B1 * | 9/2002 | Divino et al. | 422/44 |

OTHER PUBLICATIONS

U.S. patent application Ser. No. 09/122,438 filed Jul. 24, 1998, Divino, Jr. et al., "Apparatus for the Preparation and Delivery of Gas–Supersaturated Fluids".

U.S. patent application Ser. No. 09/312,181 filed May 14, 1999, Buhr et al., "Apparatus and Method for High Pressure Fluid Filtration".

Padmavathy Guttikonda et al., "Effect of Topical O2–Supersaturated Normal Saline on UV Light–Induced Mouse Ear Inflammation," SSID Dermatology Session Abstract, vol. 44, No. 1, p. 51A, Jan. 1996.

B. Kantor et al., "Coronary Repersusion with Aqueous Oxygen Improves Left Ventricular Ejection Fraction and May Reduce Mortality in an Ischemic Porcine Model," (Abstracts/Poster TCT–231), Amer. J. Cardiology, p. 86S, Oct. 8, 1998.

S. C. Davis et al., "Delivery of Oxygen to Cutaneous Tissue Via a Super Saturated Oxygen (SOS) Emulsions," Journal of Investigative Dermatology, vol. 112, No. 4, p. 632, Apr. 1999.

N.M. Yusof et al., "Assessment of the Safety and Efficacy of Supersaturated Oxygen Solution: A Novel Method of Reducing Myocardial Ischemia in PTCA,"(Abstracts/Poster TCT–276), Amer. J. Cardiology, p. 100S, Oct. 8, 1998.

John Metschl, "The Supersaturation of Gases in Water and Certain Organic Liquids," vol. 28, pp. 417–437, 1924.

Frank B. Kenrick et al., "Supersaturation of Gases in Liquids," J. Phys. Chem., vol. 28, pp. 1308–1315, 1924.

Robert B. Dean, "The Formation of Bubbles," Journal of Applied Physics, vol. 15, pp. 446–451, May, 1944.

K.E. Karlson et al., "Total cardiopulmonary bypass with a new microporous Teflon membrane oxygenator," Surgery, vol. 76, No. 6, pp. 935–945, Dec. 1974.

W. Zingg et al., "Improving the Efficiency of a Tubular Membrane Oxygenator," Med. Progr. Technol. 4, pp. 139–145, 1976.

C. Boe et al., "Use of Hyperbaric Oxygen as Oxygen Source in Extracorporeal Oxygenation of Blood," Physiological and Clinical Aspects of Oxygenator Design, Elsevier North–Holland Biomedical Press, Luxembourg, 1976.

Pieter Stroev et al., "Supersaturated fluorocarbon as an oxygen source," Physiological and Clinical Aspects of Oxygenator Design, Elsevier North–Holland Biomedical Press, pp. 129–139, Luxembourg, 1976.

Edvard A. Hemmingsen, "Cavitation in gas–supersaturated solutions," Journal of Applied Physics, vol. 46, No. 1, pp. 213–218, Jan. 1976.

Robert H. Bartlett et al., "Instrumentation for cardiopulmonary bypass—past, present, and future," Medical Instrumentation, vol. 10, No. 2, pp. 119–124, Mar.–Apr. 1976.

Wayne A. Gerth et al., "Gas Supersaturation Thresholds for Spontaneous Cavitation in Water with Gas Equilibration Pressures up to 570 atml," Z. Naturforsch, 31a, pp. 1711–1716, Oct. 5, 1976.

Armand A. Lefemine et al., "Increased oxygen pressure to improve the efficiency of membrane oxygenators," Medical Instrumentation, vol. 10, No. 6, pp. 304–308, Nov.–Dec. 1976.

Edvard A. Hemmingsen, "Effects of Surfactants and Electrolytes on the Nucleation of Bubbles in Gas–Supersaturated Solutions," Z. Naturforsch, 33a, pp. 164–171, Oct. 25, 1977.

Philip A. Drinker et al., "Engineering Aspects of ECMO Technology," Artificial Organs, vol. 2, No. 1, pp. 6–11, Feb. 1978.

Robert C. Eberhart et al., "Mathematical and Experimental Methods for Design and Evaluation of Membrane Oxygenators," Artificial Organs, vol. 2, No. 1, pp. 19–34, Feb. 1978.

S. Marlow et al., "A $pO_2$ Regulation System For Membrane Oxygenators," American Society For Artificial Internal Organs, vol. XXVII, pp. 299–303, 1981.

E.H. Spratt et al., "Evaluation of a Membrane Oxygenator For Clinical Cardiopulmonary Bypass," Trans Am Soc Artif Intern Organs, vol. XXVII, pp. 285–288, 1981.

F. Valdée et al., "Ex Vivo Evaluation of a New Capillary Membrane Oxygenator," Trans Am Soc Artif Intern Organs, vol. XXVII, pp. 270–275, 1981.

T. Dohi et al., "Development and Clinical Application of a New Membrane Oxygenator Using a Microporous Polysulfone Membrane," Trans J. Mieszala et al., "Evaluation of a New Low Pressure Drop Membrane Oxygenator," Trans Am Soc Artif Intern Organs, vol. XXVIII, pp. 342–349, 1982.

S. Ohtake et al., "Experimental Evaluation of Pumpless Arteriovenous ECMO With Polypropylene Hollow Fiber Membrane Oxygenator for Partial Respiratory Support," Trans Am Soc Artif Intern Organs, vol. XXIX, pp. 237–241, 1983.

F.M. Servas et al., "High Efficiency Membrane Oxygenator," Trans Am Soc Artif Intern Organs, vol. XXIX, pp. 231–236, 1983.

Karl E. Karlson et al., "Initial Clinical Experience With a Low Pressure Drop Membrane Oxygenator for Cardiopulmonary Bypass in Adult Patients," The American Journal of Surgery, vol. 147, pp. 447–450, Apr. 1984.

H. Matsuda et al., "Evaluation of a New Siliconized Polypropylene Hollow Fiber Membrane Lung for ECMO," Trans Am Soc Artif Intern Organs, vol. XXXI, pp. 599–603, 1985.

T. Kawamura et al., "ECMO in pumpless RV to LA bypass," Trans Am Soc Artif Intern Organs, vol. XXXI, pp. 616–621, 1985.

J.B. Zwischenberger et al., "Total Respiratory Support With Single Cannula Venovenous ECMO: Double Lumen Continuous Flow vs. Single Lumen Tidal Flow," Trans Am Soc Artif Intern Organs, vol. XXXI, pp. 610–615, 1985.

Yehuda Finkelstein et al., "Formation of Gas Bubbles in Supersaturated Solutions of Gases in Water," AIChE Journal, vol. 13, No. 9, pp. 1409–1419, Sep., 1985.

Mordecai B. Rubin et al., "Measurements of Critical Supersaturation for Homogeneous Nucleation of Bubbles," American Chemical Society, Dec. 9, 1986.

"Fluosol® 20% Intravascular perfluorochemical Emulsion Product Information," Alpha Therapeutic Corporation, Los Angeles, California, pp. 1–8, Dec. 1989.

Yehuda Tamari et al., "The Effect of High Pressure on Microporous Membrane Oxygenator Failure," Artificial Organs, vol. 15, No. 1, pp. 15–22, Feb. 1991.

J. Richard Spears et al., "Potential Intravascular Oxygenation with Oxygen Clathrate Hydrate," (Abstract 388), Abstracts From the $65^{th}$ Scientific Sessions, Circulation, vol. 80, Suppl. I, p. I–97, 1992.

Brian A. Cason, et al., "Effects of High Arterial Oxygen Tension on Function, Blood Flow Distribution, and Metabolism in Ischemic Myocardium," Circulation, vol. 85, No. 2, pp. 828–838, Feb. 1992.

Taijiro Sueda et al., "Evaluation of Two New Liquid–Liquid Oxygenators," ASAIO Journal, pp. 923–928, 1993.

JDS Gaylor et al., "Membrane oxygenators: influence of design on performance," Perfusion, vol. 9, No. 3, pp. 173–180, 1994.

Brian A. Cason et al., "Therapeutic Hyperoxia Diminishes Myocardial Stunning," J Card Surg, pp. 459–464, 1994.

Michael T. Snider et al., Small Intrapulmonary Artery Lung Prototypes: Design, Construction, and In Vitro Water Testing, ASAIO Journal, pp. M533–M539, 1994.

Terry G. Campbell, Changing Criteria for the Artificial Lung Historic Controls on the Technology of ECMO,: ASAIO Journal, vol. 40, No. 2, pp. 109–120, Apr.–Jun. 1994.

Steven N. Vaslef, et al., "Design and Evaluation of a New, Low Pressure Loss, Implantable Artificial Lung," ASAIO Journal, vol. 40, No. 3, pp. M522–M526, Jul.–Sep. 1994.

Philip D. Beckley, et al., "Comparison of the performance characteristics of three generations of membrane oxygenators: Univox®, Univox®Gold™ and SpiralGold™," Perfusion, vol. 11, No. 1, pp. 61–70, 1996.

J. Richard Spears et al., "Myocardial Protection With a Perfusion Guidewire During Balloon Angioplasty in a Canine Model," (Abstracts/Poster 1032-30), JACC, vol. 27, Suppl. A, p. 392A, Feb. 1996.

J. Richard Spears, "Advances in the Management of Respiratory Failure—Aqueous Preparations of Oxygen," American Society for Artificial Internal Organs, Inc., vol. 42, No. 3, May–Jun., 1996.

Kane M. High et al., "Polysulfone Coating for Hollow Fiber Artificial Lungs Operated at Hypobaric and Hyperbaric Pressures," ASAIO Journal, vol. 42, No. 5, pp. M442–M445, Sep.–Oct. 1996.

J. Richard Spears et al., "Hyperoxemic Perfusion with Aqueous Oxygen Improves LV Function During Experimental M1–Reperfusion," (Abstract 2038), Circulation, vol. 96, Abstracts from the 70$^{th}$ Scientific Sessions, Supplement I, pp. I–364–I–365, 1997.

Richard Maas et al., "Superoxygenation Process Treats Highly Concentrated Wastewaters," WATER/Engineering & Management, pp. 29–33, 39, Feb. 1997.

J.R. Spears et al., "Intraaortic Infusion of Oxygen in a Rabbit Model," (Abstracts/Poster 1014–155), JACC, vol. 29, Suppl. A, pp. 317A–318A, Feb. 1997.

K. Minami et al., "Pulsatile and nonpulsatile extracorporeal circulation using Capiox®E Terumo oxygenator: a comparison study with Ultrox® and Maxima® membrane oxygenators," The Journal of Cardiovascular Surgery, vol. 38, No. 3, pp. 227–232, Jun. 1997.

Adrian H. Shandling et al., "Hyperbaric oxygen and thrombolysis in myocardial infarction: The "HOT MI" Pilot Study," American Heart Journal, vol. 134, No. 3, pp. 544–550, Sep. 1997.

J. Richard Spears et al. Aqueous Oxygen: A Highly $O_2$–Supersaturated infusate for Hyperoxemic Treatment of Postischemic Myocardium, (Abstract/Poster TCT–262), The American Journal of Cardiology, Sep. 1997.

Yoshinari Niimi et al, "Effects of Ultrathin Silicone Coating of Porous Membrane on Gas Transfer and hemolytic Performance," Artificial Organs, vol. 21, No. 10, pp. 1082–1086, Oct. 1997.

J. Richard Spears et al., "Aqueous Oxygen—A Highly $O_2$–Supersaturated Infusate for Regional Correction of Hypoxemia and Production of Hyperoxemia," Circulation, vol. 96, No. 12, pp. 4385–4391, Dec. 16, 1997.

G.J. Brereton et al., "Nucleation in small capillary tubes," Chemical Physics 230, pp. 253–265, 1998.

David W. Fried, et al., "Clinical oxygen transfer comparison of the Terumo Capiox SX18 and SX25 membrane oxygenators," Perfusion, vol. 13, No. 2, pp. 119–127, 1998.

J.R. Spears et al., "Hyperoxemic Reperfusion With Aqueous Oxygen Improves Left Ventricular Function and Microvascular Flow in the Postischemic Canine Myocardium," (Abstract 1185–127), JACC, vol. 31 (Suppl. A) p. 449A, Feb. 1998.

Cassandra Henney et al., "Post MI Aqueous Oxygen Hyperoxemic Coronary Reperfusion Acutely Improves Canine LV Function Compared to Normoxemic Reperfusion," (Abstracts/Poster TCT–277), Amer. J. Cardiology, p. 100S, Oct. 8, 1998.

J. Richard Spears et al., "Subselective Intracoronary Aqueous Oxygen Hyperoxemic Reperfusion After One Hour Coronary Occlusion in Swine Restores Left Ventricular Function," (Abstracts/Poster 1124–165), JACC, vol. 33, Suppl. A, p. 357A, Feb. 1999.

Product Monograph, Fluosol® 20% Intravascular Perfluorochemical Emulsion, "Delivers Oxygen to Protect the Heart During PTCA," Alpha Therapeutic Corporation, pp. 3–30.

E. Newton Harvey et al., "Bubble Formation In Animals," J. Cell. Comp. Physiol., vol. 24, pp. 23–34.

* cited by examiner

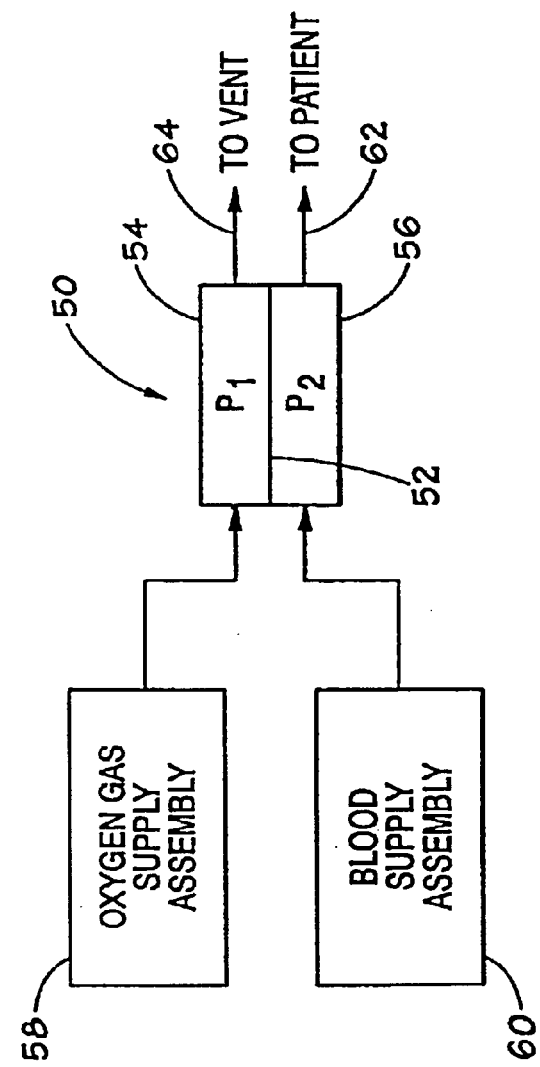

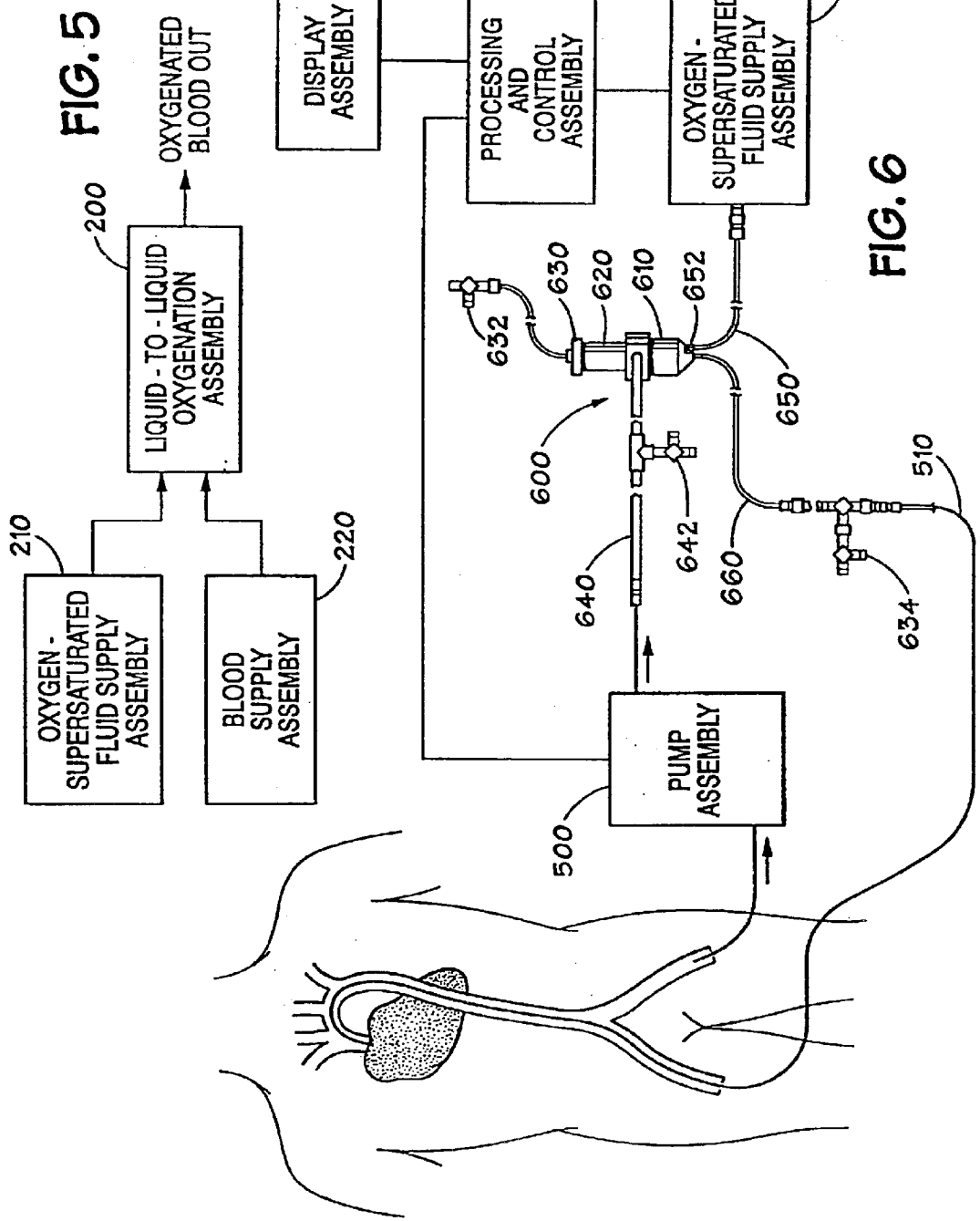

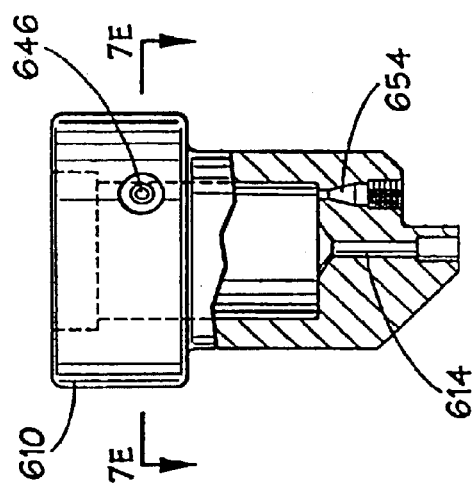
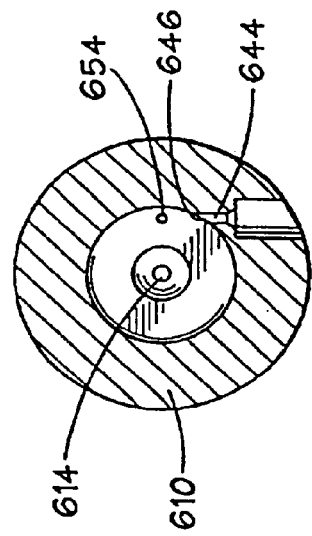
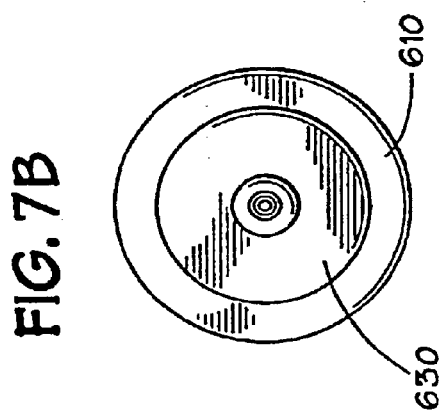
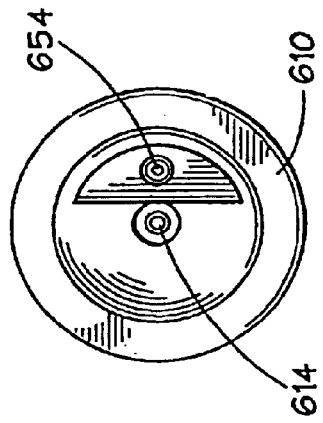
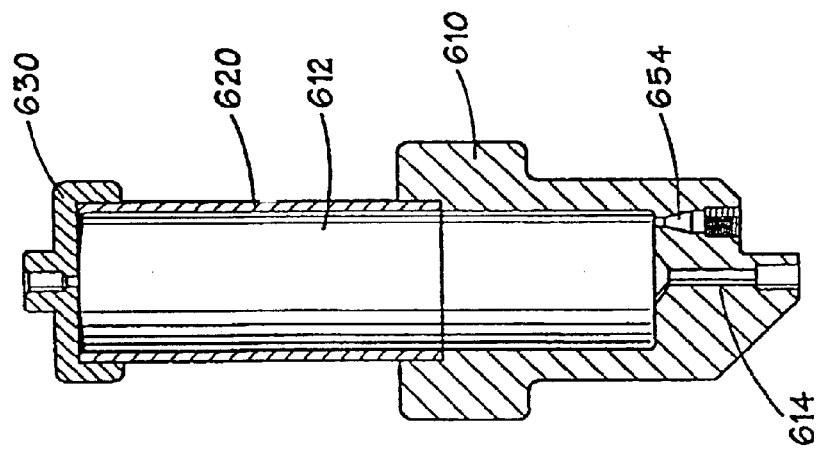

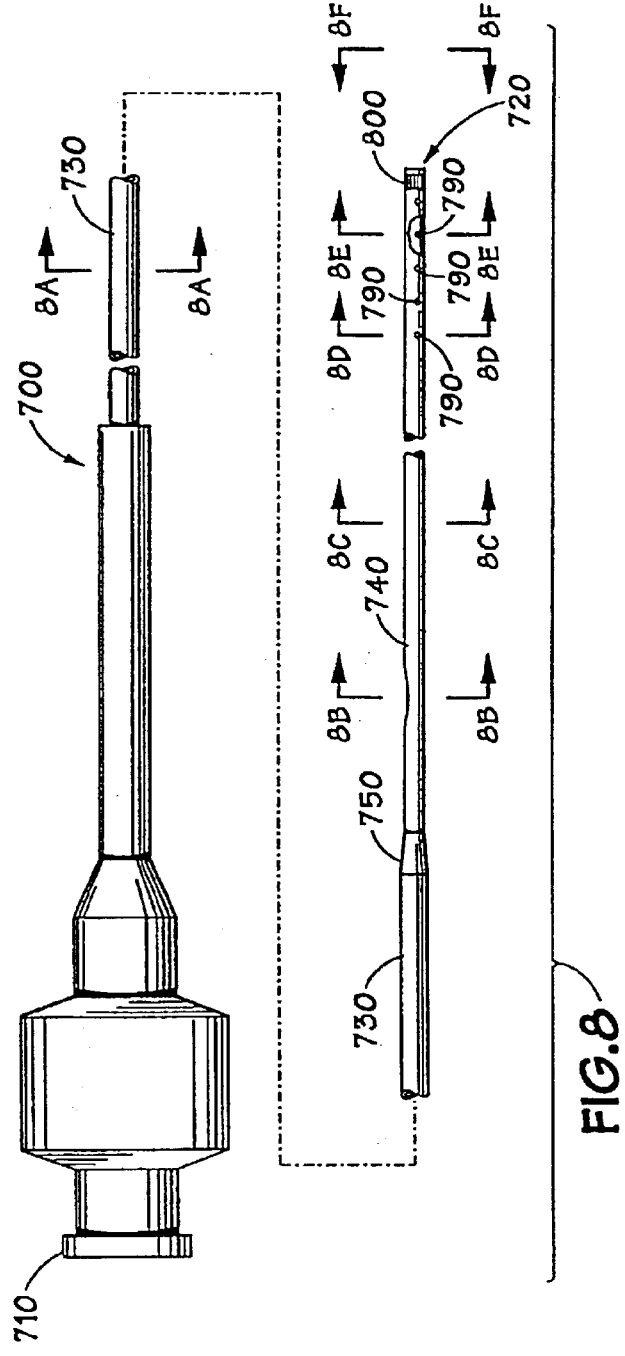

APPARATUS AND METHOD FOR BLOOD OXYGENATION

FIELD OF THE INVENTION

The present invention relates generally to a system and method for oxygenating blood, and more particularly, to a system and method for providing oxygenated blood, e.g., hyperoxemic or hyperbaric blood, to a patient.

BACKGROUND OF THE INVENTION

Oxygen is a crucial nutrient for human cells. Cell damage may result from oxygen deprivation for even brief periods of time, which may lead to organ dysfunction or failure. For example, heart attack and stroke victims experience blood flow obstructions or diversions that prevent oxygen from being delivered to the cells of vital tissues. Without oxygen, the heart and brain progressively deteriorate. In severe cases death results from complete organ failure. Less severe cases typically involve costly hospitalization, specialized treatments and lengthy rehabilitation.

Blood oxygen levels may be described in terms of the concentration of oxygen that would be achieved in a saturated solution at a given partial pressure of oxygen ($pO_2$). Typically, for arterial blood, normal blood oxygen levels (i.e., normoxia or normoxemia) range from 90–110 mm Hg. Hypoxemic blood (i.e., hypoxemia) is arterial blood with a $pO_2$ less than 90 mm Hg. Hyperoxic blood (i.e., hyperoxemia or hyperoxia) is arterial blood with a $pO_2$ greater than 400 mm Hg (see Cason et. al (1992) Effects of High Arterial Oxygen Tension on Function, Blood Flow Distribution, and Metabolism in Ischemic Myocardium, *Circulation*, 85(2):828–38, but less than 760 mm Hg (see Shandling et al. (1997) Hyperbaric Oxygen and Thrombolysis in Myocardial Infarction: The "HOT MI" Pilot Study, *American Heart Journal* 134(3):544–50). Hyperbaric blood is arterial blood with a $pO_2$ greater than 760 mm Hg. Venous blood typically has a $pO_2$ level less than 90 mm Hg. In the average adult, for example, normal venous blood oxygen levels range generally from 40 mm Hg to 70 mm Hg.

Blood oxygen levels also might be described in terms of hemoglobin saturation levels. For normal arterial blood, hemoglobin saturation is about 97% and varies only slightly as $pO_2$ levels increase. For normal venous blood, hemoglobin saturation is about 75%

In patients who suffer from acute myocardial infarction, if the myocardium is deprived of adequate levels of oxygenated blood for a prolonged period of time, irreversible damage to the heart can result. Where the infarction is manifested in a heart attack, the coronary arteries fail to provide adequate blood flow to the heart muscle.

Treatment of acute myocardial infarction or myocardial ischemia often comprises performing angioplasty or stenting of the vessels to compress, ablate or otherwise treat the occlusion(s) within the vessel walls. For example, a successful angioplasty uses a balloon to increase the size of the vessel opening to allow increased blood flow.

Even with the successful treatment of occluded vessels, a risk of tissue injury may still exist. During percutaneous transluminal coronary angioplasty (PTCA), the balloon inflation time is limited by the patient's tolerance to ischemia caused by the temporary blockage of blood flow through a vessel during balloon inflation. Reperfusion injury also may result, for example, due to slow coronary reflow or no reflow following angioplasty.

For some patients angioplasty procedures are not an attractive option for the treatment of vessel blockages. Such patients typically are at increased risk of ischemia for reasons such as poor left ventricular function, lesion type and location, or the amount of the myocardium at risk. The treatment options for such patients thus include more invasive procedures such as coronary bypass surgery.

To reduce the risk of tissue injury typically associated with treatments of acute myocardial infarction and myocardial ischemia, it is usually desirable to deliver oxygenated blood or oxygen-enriched fluids to at-risk tissues. Tissue injury is minimized or prevented by the diffusion of the dissolved oxygen from the blood or fluids to the tissue and/or blood perfusion that removes metabolites and that provides other chemical nutrients.

In some cases, the desired treatment of acute myocardial infarction and myocardial ischemia includes perfusion of oxygenated blood or oxygen-enriched fluids. During PTCA, for example, tolerated balloon inflation time may be increased by the concurrent introduction of oxygenated blood into the patient's coronary artery. Increased blood oxygen levels also may cause the normally perfused left ventricular cardiac tissue into hypercontractility to further increase blood flow through the treated coronary vessels.

The infusion of oxygenated blood or oxygen-enriched fluids also may be continued following the completion of PTCA treatment or other procedures (e.g. surgery) wherein cardiac tissue "stunning" with associated function compromise has occurred. In some cases continued infusion may accelerate the reversal of ischemia and facilitate recovery of myocardial function.

Conventional methods for the delivery of oxygenated blood or oxygen-enriched fluids to at-risk tissues involve the use of blood oxygenators. Such procedures generally involve withdrawing blood from a patient, circulating it through an oxygenator to increase blood oxygen concentration, and then delivering the blood back to the patient. One example of a commercially available blood oxygenator is the Maxima blood oxygenator manufactured by Medtronic, Inc., Minneapolis, Minn.

There are drawbacks, however, to the use of a conventional oxygenator in an extracorporeal circuit for oxygenating blood. Such systems typically are costly, complex and difficult to operate. Often a qualified perfusionist is required to prepare and monitor the system.

Conventional oxygenator systems also typically have a large priming volume, i.e., the total volume of blood contained within the oxygenator, tubing and other system components, and associated devices. It is not uncommon in a typical adult patient case for the oxygenation system to hold more than one to two liters of blood. Such large priming volumes are undesirable for many reasons. For example, in some cases a blood transfusion may be necessary to compensate for the blood temporarily lost to the oxygenation system because of its large priming volume. Heaters often must be used to maintain the temperature of the blood at an acceptable level as it travels through the extracorporeal circuit. Further, conventional oxygenator systems are relatively difficult to turn on and off. For instance, if the oxygenator is turned off, large stagnant pools of blood in the oxygenator might coagulate.

In addition, with extracorporeal circuits including conventional blood oxygenators there is a relatively high risk of inflammatory cell reaction and blood coagulation due to the relatively slow blood flow rates and the large blood contact surface area. A blood contact surface area of about 1–2 $m^2$ and velocity flows of about 3 cm/s are not uncommon with conventional oxygenator systems. Thus, relatively aggressive anti-coagulation therapy, such as heparinization, is usually required as an adjunct to using the oxygenator.

Perhaps one of the greatest disadvantages to using conventional blood oxygenation systems is that the maximum partial pressure of oxygen ($pO_2$) that can be imparted to blood with commercially available oxygenators is about 500 mm Hg. Thus, blood $pO_2$ levels near or above 760 mm Hg cannot be achieved with conventional oxygenators.

Some experimental studies to treat myocardial infarction have involved the use of hyperbaric oxygen therapy. See, e.g., Shandling et al. (1997), Hyperbaric Oxygen and Thrombolysis in Myocardial Infarction: The "HOT MI" Pilot Study, *American Heart Journal* 134(3):544–50. These studies generally have involved placing patients in chambers of pure oxygen pressurized at up to 2 atmospheres, resulting in systemic oxygenation of patient blood up to a $pO_2$ level of about 1200 mm Hg. However, use of hyperbaric oxygen therapy following restoration of coronary artery patency in the setting of an acute myocardial infarction is not practical. Monitoring critically ill patients in a hyperbaric oxygen chamber is difficult. Many patients become claustrophobic. Ear damage may occur. Further, treatment times longer than 90 minutes cannot be provided without concern for pulmonary oxygen toxicity.

For these reasons, the treatment of regional organ ischemia generally has not been developed clinically. Thus, there remains a need for a simple and convenient system for delivering oxygenated blood and other fluids to patients for the localized prevention of ischemia and the treatment of post-ischemic tissue and organs.

SUMMARY OF THE INVENTION

The present invention may address one or more of the problems set forth above. Certain possible aspects of the present invention are set forth below as examples. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present invention, a system for the preparation and delivery of oxygenated blood is provided. In applications involving the prevention of ischemia or the treatment of ischemic tissues, the system may be used for the preparation and delivery of oxygenated blood to a specific location within a patient's body. The system may include an extracorporeal circuit for oxygenating blood, e.g., increasing the level of oxygen in the blood, in which the blood to be oxygenated is blood withdrawn from the patient. The system also may be used advantageously for regional or localized delivery of oxygenated blood.

Factors influencing the determination of blood flow characteristics for the extracorporeal circuit may include one or more of the many clinical parameters or variables of the oxygenated blood to be supplied to the patient, e.g., the size of the patient, the percentage of overall circulation to be provided, the size of the target to be accessed, hemolysis, hemodilution, $pO_2$, pulsatility, mass flow rate, volume flow rate, temperature, hemoglobin concentration and pH.

Interventional Devices (Catheters, Infusion Guidewires, etc.)

The system may comprise a delivery assembly including an elongated, generally tubular assembly including a central lumen and at least one end placeable within a patient body proximate a tissue site to be treated, the end including an outlet port for the oxygenated blood. The delivery assembly advantageously comprises a catheter defining a fluid pathway, including a proximal portion adapted for coupling to an oxygenated blood supply assembly, and a distal portion defining a fluid pathway removably insertable within a patient's body, for infusing the oxygenated blood to predetermined sites. Alternatively, the delivery assembly may comprise an infusion guidewire, sheath, or other similar interventional device of the type used to deliver fluids to patients.

The embodiments may be used in conjunction with angiographic or guiding catheters, arterial sheaths, and/or other devices used in angioplasty and in other interventional cardiovascular procedures. The system may be used in applications involving one or more vascular openings, i.e., in either contralateral or ipsilateral procedures.

In contralateral procedures blood is withdrawn from the patient at a first location, e.g., the left femoral artery. The oxygenated blood is returned to the patient at a second location proximate the tissue to be treated. Blood oxygenation occurs as the blood pumped through the extracorporeal circuit or loop passes through an oxygenation assembly and forms the oxygenated blood to be delivered. In applications where the system includes a catheter, the catheter may include a distal end removably insertable within a patient's body through a second location, such as the patient's right femoral artery. The distal end includes at least one port in fluid communication with the central lumen and through which the oxygenated blood may exit. Further, the distal portion of the catheter may be adapted with a tip portion shaped so as to promote insertion of the device, such as through the same sheath used for interventional procedures like angioplasty, to specific predetermined locations within a patient's body. Examples of tip portion shapes which may be used include any of the standard clinically accepted tip configurations used with devices like guide catheters for providing access to and for holding in locations like the coronary ostium. Accordingly, the method may further include the step of positioning the portion of the distal end of the catheter including the fluid exit port at a predetermined location within a patient body proximate to the tissue to be treated.

In ipsilateral procedures, the system may be used along with one or more of any of a number of suitable, standard-size, clinically accepted guide catheters and/or introducer sheaths. The system, for example, may comprise a catheter, a catheter and guide catheter, or a catheter and sheath, for use within a guide catheter or introducer sheath used for the primary interventional procedure.

The delivery assembly advantageously comprises a catheter suitable for sub-selective delivery of the oxygenated blood. However, the catheter embodiment selected for use will depend upon the circumstances involved in a particular application. For example, in some cases involving the prevention of myocardial ischemia or the treatment of ischemic myocardial tissues, a selective or non-selective catheter may be preferred.

The delivery of oxygenated blood may occur via a "simple" interventional device (e.g., a catheter or infusion guidewire) or a delivery device or lumen associated with or forming a part of a multiple-component assembly operable for the performance of diagnostic and/or therapeutic procedures (i.e., in addition to the delivery of oxygenated blood). Examples of such assemblies include, without limitation, devices for the placement of stents, angioplasty balloon catheters, radiation delivery systems, drug delivery devices, etc. Flow rates of about 25 ml/min to about 200 ml/min for the oxygenated blood may be advantageous, particularly about 75 ml/min to about 125 ml/min.

Fluid Delivery Pathways

Advantageously, oxygenated blood is provided to a particular desired location by a fluid delivery apparatus including: (1) a generally elongated fluid delivery assembly having a proximal section and a distal section, the distal section including a portion at least partially removably insertable within a patient's body, the removably insertable portion including at least one fluid exit port in fluid communication with a fluid delivery lumen extending between the proximal section and the removably insertable portion of the fluid delivery assembly; and (2) a fluid conduit having: a first end portion for receiving a supply of blood at the outlet of a blood pump operably coupled to the fluid conduit; a second end releasably coupled to the fluid delivery lumen of the fluid delivery assembly; and an intermediate portion between the first and second ends adapted for oxygenating the supply of blood; the fluid conduit and the fluid delivery lumen defining a continuous fluid pathway between the first end portion of the fluid conduit and the fluid exit port(s). Advantageously, the fluid delivery apparatus provides oxygenated blood, and most advantageously hyperoxemic or hyperbaric blood, to a patient without potentially clinically significant gas bubbles in the blood. More advantageously, the fluid delivery apparatus can provide to a patient oxygenated blood having a $pO_2$ greater than about 760 mm Hg but less than $pO_{2max}$ for a given blood flow rate $Q_{blood}$, where $pO_{2max}$ equals the maximum back pressure generated within the fluid delivery apparatus by operation of the blood pump to achieve the flow rate $Q_{blood}$.

In one embodiment, the intermediate portion of the fluid conduit adapted for oxygenating the blood supplied by the blood pump, i.e., the oxygenation assembly, comprises a high pressure membrane oxygenator. In another embodiment, the fluid conduit intermediate portion comprises an assembly including a mixing region in which an oxygenated fluid, e.g., an oxygen-supersaturated fluid, combines with the blood to effect direct liquid-to-liquid oxygenation. In a further embodiment, the intermediate portion may comprise an assembly for combining two fluid streams (e.g., an apparatus generally resembling a y-tube, t-adaptor, or the like), the assembly adapted for coupling to delivery systems for supplying blood to be oxygenated and for supplying oxygenated blood or other fluids.

Accordingly, the fluid delivery apparatus advantageously may comprise a first tube portion extending between a blood pump and an oxygenation assembly; the oxygenation assembly; a second tube portion extending between the oxygenation assembly and the proximal end of a fluid delivery assembly; and the fluid delivery assembly.

In a patient breathing air through the lungs, the dissolved gases in the patient's blood (nitrogen, N2; carbon dioxide, CO2; and oxygen, O2) equal atmospheric pressure. Chemically, this relationship is noted by the equation $$P_{total} = pN_2 + pCO_2 + pO_2$$

where $P_{total}$ is atmospheric pressure and the right-hand side of the equation shows the relative, or partial, pressures of the dissolved gases in air. The above equation is balanced approximately as follows:

760 mm Hg=600 mm Hg+45 mm Hg+115 mm Hg

For $P_{blood}$ including dissolved gases having the partial pressures put forth above, during a hyperoxygenation process occurring at the intermediate portion of the fluid conduit the $pO_2$ is raised and $P_{total}$ can exceed atmospheric pressure. For example, if the $pO_2$ increases to 800 mm Hg without change to pN2 and pCO2, then $P_{total}$ would equal 1445 mm Hg, a nearly two-fold increase.

The fluid pressure at the outlet of the intermediate portion of the fluid conduit, $P_{fluid}$, is a measure of the pressure differential across the portion of the fluid conduit between that location and the fluid exit port(s) plus the outlet pressure. To avoid the formation of potentially clinically significant gas bubbles, it is particularly advantageous to raise the fluid pressure at the outlet of the intermediate portion of the fluid conduit to a level that exceeds the total dissolved gas pressure. Thus, delivery of oxygenated blood may occur bubble-free, i.e., without the formation of potentially clinically significant bubbles, where $P_{fluid} > P_{total}$.

Because most pressure measurements use gauge pressures (i.e., gauge pressure=total pressure minus atmospheric pressure), the relationship for bubble-free delivery also may be simplified and approximated to $\Delta P_{fluid} > pO_{2(out)}$, where $pO_{2(out)}$ is the $pO_2$ of the oxygenated blood to be delivered to the patient. In other words, a caregiver might need only compare two simple measurements, $\Delta P_{fluid}$ and $pO_{2(out)}$, to ensure bubble-free delivery during a procedure.

Experimental data supports use of the simplified and approximated relationship $\Delta P_{fluid} > pO_{2(out)}$ for achieving bubble-free delivery. As shown in Table I, a fluid delivery apparatus including a liquid-to-liquid oxygenation assembly was used with two catheters having different effective diameters to infuse oxygenated blood into the left coronary vasculature of a 40 kg swine to determine whether the relationship between $\Delta P_{fluid}$ and $pO_{2(out)}$ affects bubble formation during oxygenated blood infusion. In trials where $\Delta P_{fluid} > pO_{2(out)}$, no bubbles were observed using 2D-echocardiography during oxygenated blood infusion, and an ultrasonic bubble detection system did not detect any bubbles of greater than about 100 μm diameter. On the other hand, in trials where $\Delta P_{fluid} < pO_{2(out)}$, 3–4 bubbles per heart beat were observed in the right atrium using 2D-echocardiography during oxygenated blood infusion, and the ultrasonic bubble detection system numerous bubbles of greater than about 100 μm diameter.

TABLE I

| Blood Flow (ml/min) | Blood/Oxygenated Fluid (dimensionless fluid flow rate ratio) | $\Delta P_{fluid}$ | $pO_{2(out)}$ | Ultrasonic Bubble Event (#) | Bubbles in 2D-Echo (#/heart beat) |
|---|---|---|---|---|---|
| 78 | 52 | 843 | 783 | 0 | 0 |
| 78 | 52 | 819 | 723 | 0 | 0 |
| 103 | 47 | 1043 | 834 | 0 | 0 |
| 104 | 35 | 1031 | 982 | 0 | 0 |
| 107 | 36 | 311 | 987 | 32 | 3–4 |
| 107 | 36 | 315 | 1031 | 15 | 3–4 |
| 152 | 51 | 449 | 771 | 24 | 3–4 |
| 152 | 51 | 460 | 741 | 69 | 3–4 |

Typically, $pO_{2(out)}$ may be selected by the caregiver based upon the circumstances involved in a particular application. Thus, bubble-free delivery may be ensured by selecting an appopriate fluid delivery apparatus, i.e., one which may effect downstream of the fluid conduit intermediate portion a fluid pressure drop that exceeds the selected target $pO_2$ for a given blood flow rate. Further, the fluid pressure drop may vary depending upon factors such as fluid delivery length and fluid lumen geometry (e.g., internal diameter, taper, cross-sectional profile, etc.), factors which may vary depending upon the specific application involved. Thus, it may prove helpful (e.g., to promote ease of selection) to characterize all or a portion of the fluid delivery apparatus downstream of the intermediate portion of the fluid conduit in terms of an effective diameter, or in terms of achievable $pO_2$ levels for a given oxygenation assembly and/or give conditions at the outlet of the intermediate portion of the fluid conduit.

For example, in accordance with one embodiment of the present invention, for an exemplary oxygenated blood fluid delivery apparatus, oxygenated blood pressure at the oxygenation assembly is a function of blood flow rate and catheter effective diameter. For an oxygenated blood fluid delivery apparatus, the relationship between blood flow rate and oxygenated blood pressure at the oxygenation assembly for a given catheter may be determined using the Hagen-Poiseuille law:

$$Q = \frac{\pi \Delta P D^4}{128 L \eta}$$

which generally governs laminar fluid flows through conduits, in which Q=volumetric flow rate; L=conduit length; D=conduit inside diameter; η=fluid viscosity; and ΔP=pressure difference across the conduit length. Other embodiments also may be used depending upon the circumstances involved in a particular application, e.g., an embodiment for turbulent flow applications, for which the relationship between blood flow rate and oxygenated blood pressure at the oxygenation assembly may be determined using models governing turbulent flow.

In general, with a given oxygenated blood fluid delivery apparatus, for a constant blood flow rate $Q_{blood}$, as the effective inner diameter of the catheter increases, the blood pressure $P_{fluid(gauge)}$ at the oxygenation assembly decreases. By knowing the simplified and approximated bubble-free delivery relationship, $\Delta P_{fluid} > pO_{2(out)}$, a caregiver having a catheter characterized by effective inner diameter may determine whether an appropriate range of blood flow rates are achievable if the caregiver were to use a fluid delivery apparatus including the catheter to deliver blood having a desired $pO_2$. Alternatively, a caregiver specifying a desired oxygenated blood $pO_2$ and oxygenated blood flow rate range may select a catheter for use in a fluid delivery apparatus for a particular application.

High Pressure Membrane Oxygenation Assemblies

In one embodiment, the system provided advantageously includes a membrane oxygenator assembly and assemblies for supplying controlled flows or supplies of oxygen gas and blood. Advantageously, the intermediate portion of the fluid conduit comprises a membrane oxygenator assembly operable at high pressures, i.e., oxygen gas and blood supply pressures within the membrane oxygenator assembly of greater than atmospheric pressure.

The assembly for supplying controlled flows or supplies of oxygen gas advantageously includes a regulated source of oxygen gas, so that oxygen gas is delivered to the membrane oxygenator assembly at a pressure greater than atmospheric pressure. Advantageously, oxygen gas is supplied to the membrane oxygenator assembly at a pressure greater than atmospheric pressure and less than about 50 p.s.i.a., the approximate maximum pressure that may be generated by commercially available blood pumps delivering blood. The assembly for supplying controlled flows or supplies of oxygen gas may be one of the many commercially available and clinically accepted oxygen delivery systems suitable for use with human patients (e.g., regulated bottled oxygen).

The assembly for supplying controlled flows or supplies of blood advantageously includes a source of blood in combination with means for providing the blood to the membrane oxygenator assembly. Advantageously, the blood to be oxygenated comprises blood withdrawn from the patient, so that the blood supply assembly includes a blood inlet disposed along a portion of a catheter or other similar device at least partially removably insertable within the patient's body; a pump loop that in combination with the catheter or other device defines a continuous fluid pathway between the blood inlet and the membrane oxygenator assembly; and a blood pump for controlling the flow of blood through the pump loop, i.e., the flow of blood provided to the membrane oxygenator assembly. The blood pump may be one of the many commercially available and clinically accepted blood pumps suitable for use with human patients. One example of such a pump is the Model 6501 RFL3.5 Pemco peristaltic pump available from Pemco Medical, Cleveland, Ohio.

The system provided advantageously includes an oxygenated blood supply assembly comprising a membrane oxygenator assembly including at least one membrane separating within the membrane oxygenator assembly the oxygen gas provided by the oxygen gas supply assembly and the blood provided by the blood supply assembly, and across which oxygen and other gases may diffuse. Advantageously, oxygen gas is provided to the "gas side" of the membrane oxygenator assembly by the oxygen gas supply assembly at a gas side pressure that is greater than atmospheric pressure; a supply of blood is provided by the blood supply assembly to the "blood side" of the membrane oxygenator assembly at a blood side pressure that is greater than the gas side pressure; and the oxygen gas and at least a portion of the supply of blood is maintained in contact with the membrane so that oxygen diffuses across the membrane and dissolves in the supply of blood.

The membrane may comprise either a solid material (e.g., silicone rubber) or a microporous material (e.g., a polymeric material, such as polypropylene). Advantageously, the blood side pressure is maintained at a higher level than the gas side pressure to prevent bulk gas flow across the membrane. However, lower blood side pressures may be used if a solid, non-porous membrane is used. The type of membrane used, and the gas and blood side pressures (which may be defined, for example, by a given pressure differential across the membrane) may vary depending upon the circumstances involved in a particular desired application.

The gas side of the membrane oxygenator assembly may be operated in either an "open" or a "closed" mode. In open mode, a gas side stream including oxygen gas provided by the oxygen gas supply assembly "sweeps" through the gas side of the membrane oxygenator assembly. During the sweep oxygen diffuses across the membrane to dissolve in the blood, and blood gases such as carbon dioxide and nitrogen may diffuse across the membrane to join the gas side stream. The gas side stream exits the membrane oxygenator assembly via a vent or other fluid exit conduit. In closed mode, the vent or other fluid exit conduit is closed so as to prevent the escape of bulk gas from the gas side of the membrane oxygenator assembly.

In an alternate embodiment, the membrane oxygenator assembly includes a gas inlet but is not adapted with a vent or other gas side stream fluid exit conduit. This alternate embodiment thus comprises a closed mode device. In closed mode operation the gas side pressure advantageously equals the pressure at which the oxygen gas supply assembly provides oxygen gas to the membrane oxygenator assembly. In open mode the gas side pressure drops through the membrane oxygenator assembly, albeit perhaps only slightly, from the pressure at which the oxygen gas supply assembly provides oxygen gas to the membrane oxygenator assembly.

The membrane oxygenator assembly advantageously is sized depending upon the circumstances involved in a particular desired application. For example, for an oxygenated blood delivery flow less than 0.3 liters per minute, an active membrane surface area of much less than two square meters (the approximate active membrane surface area for a conventional adult size oxygenator capable of handling six liters of blood per minute) is required. By way of example only, and without limitation on the scope of the present invention, factors affecting membrane oxygenator assembly sizing include the desired oxygen level for the blood to be oxygenated and oxygenated blood flow rate.

The system provided advantageously delivers oxygenated blood from the membrane oxygenator assembly to a given site without the formation or release of clinically significant oxygen bubbles. Delivery of oxygenated blood at a given site without clinically significant bubble formation or release advantageously may be accomplished through the selection of a catheter material, the use of an appropriately sized delivery catheter, and/or the conditioning of the same to eliminate nucleation sites. The exact material, size and conditioning procedure may vary depending upon the circumstances involved in a particular application. By way of example only, and without limitation as to the scope of the present invention, for the delivery of about 3 ml/sec of oxygenated blood with a membrane oxygenator assembly operating with a gas side pressure of about 50 p.s.i., a catheter having a length of about 130 cm and inside diameter of about 40 mils would provide a gradual pressure reduction which may help prevent the release of potentially clinically significant gas bubbles.

In another embodiment, a method is provided for the preparation and delivery of oxygenated blood. A method for enriching blood with oxygen is provided comprising providing a membrane having first and second sides; providing in contact with the first side of the membrane oxygen gas at a pressure P1 that is greater than atmospheric pressure; providing on the second side of the membrane a supply of blood at a pressure P2 that is greater than P1; and maintaining at least a portion of the supply of blood in contact with the second side of the membrane so that oxygen diffuises across the membrane and dissolves in the supply of blood. Advantageously, the pressure P1 is greater than atmospheric pressure and less than about 50 p.s.i.a. The method advantageously further comprises providing in contact with the first side of the membrane a stream including oxygen gas. Advantageously, the stream maintains contact with the first side of the membrane so that a gas (e.g., carbon dioxide, nitrogen, water vapor, etc.) in the supply of blood diffuses across the membrane and joins the stream.

In accordance with another embodiment, a method is provided for delivering oxygenated blood to a specific site within a patient's body. The method comprises raising the $pO_2$ level of blood to be supplied to the patient and the delivery of such blood to a given site. The method may include the step of controlling or providing controlled amounts of blood and oxygen gas to a membrane oxygenator assembly so as to produce oxygenated blood for delivery to a specific predetermined site. Blood oxygen levels (e.g., $pO_2$) may be maintained, adjusted, or otherwise controlled by controlling the flow rates or by providing controlled amounts of the blood and/or oxygen gas. Thus, a blood-gas control method is provided.

Liquid-to-Liquid Oxygenation Assemblies

In another embodiment, the intermediate portion of the fluid conduit adapted for oxygenating the blood supplied by the blood pump comprises an assembly including a mixing region in which an oxygenated fluid, e.g., an oxygen-supersaturated fluid, combines with the blood. Advantageously, the mixing region is defined by a chamber-like assembly including an injection zone in which the oxygenated fluid mixes with the blood at a higher pressure than the target $pO_2$ for the blood. Oxygenation of the blood occurs as a result of convective mixing involving the two contacting fluids and to a lesser extent as a result of oxygen diffusing directly from the oxygenated liquid to the blood, i.e., dispersion. The mixing advantageously is a convective mixing that occurs rapidly and completely.

In one embodiment, the chamber-like assembly comprises a mixing chamber including a generally elongated cylindrically-shaped or tubular assembly having upper and lower ends, each end having a cap or similar device fixedly attached thereto, so as to define an interior space therein. Advantageously, the mixing chamber includes in fluid communication with the interior space a first inlet port adapted for receiving a supply of blood to be oxygenated; a second inlet port adapted for receiving a supply of oxygenated fluid to be mixed with the blood; and an exit port adapted for delivery of the oxygenated blood to a particular desired location.

To promote mixing of the blood and oxygenated fluid within the chamber interior space, the blood to be oxygenated advantageously enters the mixing chamber from a location and in a direction so that a vortical or cyclonic flow of blood is created within the chamber. Advantageously, the blood enters the chamber along a path substantially tangential to the chamber wall. Advantageously, the oxygenated liquid enters the chamber proximate the blood inlet, and the oxygenated blood exits the chamber through a port in the bottom of the chamber. More advantageously, the oxygenated liquid enters the chamber in a generally upward direction normal to the initial direction of travel of the blood entering the chamber.

The mixing chamber advantageously is pressurizeable, with the lower portion of the chamber accumulating a supply of blood and the upper portion including a gas head. The gas head advantageously helps dampen the pulsatility of the blood entering the chamber.

The oxygenated fluid advantageously comprises an oxygen-supersaturated fluid in which the dissolved oxygen content would occupy a volume of between about 0.5 and about 3 times the volume of the solvent normalized to standard temperature and pressure. Examples of solvents which may be used include saline, lactated Ringer's, and other aqueous physiologic solutions. The oxygenated fluid advantageously is delivered to the mixing chamber via one or more capillaries having an internal diameter in the range of about 15 to about 700 µm (advantageously, about 100 µm), the capillaries forming a continuous fluid flow pathway between the mixing chamber and a supply or an assembly for providing a supply of the oxygenated fluid.

The oxygenated fluid typically will be supplied to the mixing chamber in accordance with parameters specified and selected by the caregiver for the desired clinical indication. The flow of oxygenated fluid is generally steady and continuous, although variable or intermittent flows may be used. Flow rates may range from about 0.1 cc/min to about 40 cc/mm, although particularly advantageous flow rates may be between about 2 cc/min and 12 cc/min. Oxygen concentrations normalized to standard temperature and pressure may range from about 0.1 ml $O_2$ per ml physiologic solution to about 3 ml $O_2$ per ml physiologic solution, although particularly advantageous concentrations may be about 1 ml $O_2$ per ml physiologic solution.

In another embodiment, a method is provided for the preparation and delivery of oxygenated blood. The method comprises providing a chamber assembly in which blood and an oxygenated liquid, e.g., an oxygen-supersaturated liquid, mix under pressure to form oxygenated blood. The method may include the step of controlling or providing controlled amounts of blood and oxygenated liquid to the chamber assembly to maintain, adjust or otherwise control blood oxygen levels. Thus, an alternate embodiment blood-gas control method is provided.

Temperature

The oxygenated blood advantageously is provided to the patient at about 37° C., i.e., system operation does not significantly affect patient blood temperature. However, in some instances, cooling of the oxygenated blood may be desired, e.g., to induce local or regional hypothermia (e.g., temperatures below about 35° C.). By way of example only, in neurological applications such cooling may be desired to achieve a neuroprotective effect. Hypothermia also may be regarded as an advantageous treatment or preservation technique for ischemic organs, organ donations, or reducing metabolic demand during periods of reduced perfusion.

Accordingly, the system provided may include a heat exchanger assembly operable to maintain, to increase, or to decrease the temperature of the oxygenated blood as desired in view of the circumstances involved in a particular application. Advantageously, temperatures for the oxygenated blood in the range of about 35° C. to about 37° C. generally will be desired, although blood temperatures outside that range (e.g., perhaps as low as 29° C. or more) may be more advantageous provided that patient core temperature remains at safe levels in view of the circumstances involved in the particular application. Temperature monitoring may occur, e.g., with one or more thermocouples, thermistors or temperature sensors integrated into the electronic circuitry of a feedback controlled system, so that an operator may input a desired perfusate temperature with an expected system response time of seconds or minutes depending upon infusion flow rates and other parameters associated with the active infusion of cooled oxygenated blood.

Examples of heat exchange assemblies suitable for use with the present system, either alone or integrated with a system component, include any of the numerous commercially available and clinically accepted heat exchanger systems used in blood delivery systems today, e.g., heat exchangers, heat radiating devices, convective cooling devices and closed refrigerant devices. Such devices may include, e:g., conductive/convective heat exchange tubes, made typically of stainless steel or high strength polymers, in contact with blood on one side and with a coolant on the other side.

In another embodiment, in a liquid-to-liquid oxygenation assembly, cooled oxygenated blood is provided by mixing blood with a cooled oxygenated liquid, e.g., an oxygen-supersaturated liquid. Any commercially available and clinically acceptable heat exchange system may be used to cool the oxygenated liquid and/or cool the oxygenated blood. Because most gases show increased solubility when dissolved into aqueous liquids at low temperatures (e.g., oxygen solubility in water increases at a rate of 1.3% per degree Celsius decrease) such a method offers the added benefit of enhanced stability of the oxygenated blood, which in some cases may enable increased oxygen concentrations.

Bubble Detection and Other Assemblies

The system may include one or more gas bubble detectors, at least one of which is capable of detecting the presence of microbubbles, e.g., bubbles with diameters of about 100 $\mu$m to about 1000 $\mu$m. In addition, the system may include one or more macrobubble detectors to detect larger bubbles, such as bubbles with diameters of about 1000 $\mu$m or more. Such macrobubble detectors may comprise any suitable commercially available detector, such as an outside, tube-mounted bubble detector including two transducers measuring attenuation of a sound pulse traveling from one side of the tube to the other. One such suitable detector may be purchased from Transonic Inc. of New York.

The microbubble and macrobubble detectors provide the physician or caregiver with a warning of potential clinically significant bubble generation. Such warnings also may be obtained through the use of transthoracic 2-D echo (e.g., to look for echo brightening of myocardial tissue) and the monitoring of other patient data.

Advantageously, the bubble detection system is able to discriminate between various size bubbles. Further, the bubble detection system advantageously operates continuously and is operatively coupled to the overall system so that an overall system shutdown occurs upon the sensing of a macrobubble.

The system also may include various conventional items, such as sensors, flow meters (which also may serve a dual role as a macrobubble detector), or other clinical parameter monitoring devices; hydraulic components such as accumulators and valves for managing flow dynamics; access ports which permit withdrawal of fluids; filters or other safety devices to help ensure sterility; or other devices that generally may assist in controlling the flow of one or more of the fluids in the system. Advantageously, any such devices are positioned within the system and used so as to avoid causing the formation of clinically significant bubbles within the fluid flow paths, and/or to prevent fluid flow disruptions, e.g., blockages of capillaries or other fluid pathways. Further, the system advantageously comprises a biocompatible system acceptable for clinical use with human patients.

BRIEF DESCRIPTION OF THE DRAWINGS

Further objects and advantages of the present invention will become apparent upon reading the following detailed description and upon referring to the accompanying drawings in which:

FIG. 1 is a schematic diagram illustrating an exemplary embodiment of a system for oxygenating blood in accordance with the present invention.

FIG. 2 is a schematic diagram illustrating an exemplary embodiment of a blood oxygenation assembly including a high pressure membrane oxygenator in accordance with the present invention.

FIG. 5 is a schematic diagram illustrating an exemplary embodiment of an oxygenation assembly including a liquid-to-liquid oxygenation assembly in accordance with the present invention.

FIG. 6 is a schematic diagram illustrating an exemplary embodiment of an extracorporeal circuit including a blood oxygenation system having a liquid-to-liquid oxygenation assembly in accordance with the present invention.

FIG. 7A is a vertical cross-sectional view of an exemplary embodiment of a liquid-to-liquid oxygenation assembly in accordance with the present invention FIG. 7B is a top view of the exemplary embodiment of the liquid-to-liquid oxygenation assembly shown in cross-sectional view in FIG. 7A.

FIG. 7C is a bottom view of the exemplary embodiment of the liquid-to-liquid oxygenation assembly shown in cross-sectional view in FIG. 7A.

FIG. 7D is a partial cut away view of the lower portion of the liquid-to-liquid oxygenation assembly shown in cross-sectional view in FIG. 7A.

FIG. 7E is a cross sectional view taken along the line E—E of the lower portion of the liquid-to-liquid oxygenation assembly shown in cross-sectional view in FIG. 7D.

FIG. 8 is a partial cut away view of an exemplary embodiment of a catheter assembly for delivery of oxygenated blood in accordance with the present invention.

FIG. 8A is a cross-sectional view of the exemplary catheter assembly shown in FIG. 8 taken along the line A—A.

FIG. 8B is a cross-sectional view of the exemplary catheter assembly shown in FIG. 8 taken along the line B—B.

FIG. 8C is a cross-sectional view of the exemplary catheter assembly shown in FIG. 8 taken along the line C—C.

FIG. 8D is a cross-sectional view of the exemplary catheter assembly shown in FIG. 8 taken along the line D—D.

FIG. 8E is a cross-sectional view of the exemplary catheter assembly shown in FIG. 8 taken along the line E—E.

FIG. 8F is an end view of the tip of the exemplary catheter assembly shown in FIG. 8.

Figure 3:
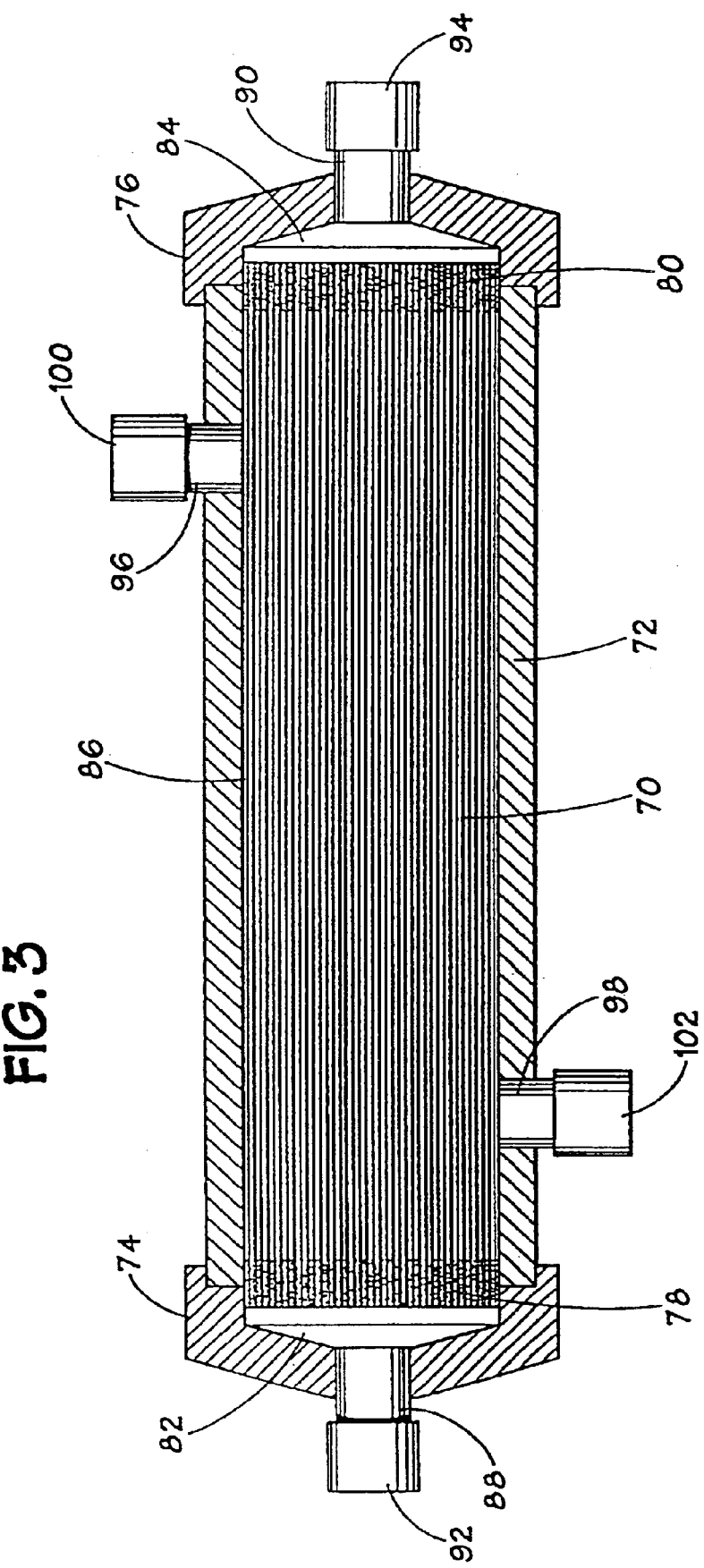
FIG. 3 is a cross-sectional view of an exemplary embodiment of a high pressure membrane oxygenator in accordance with the present invention.

The present invention may be susceptible to various modifications and alternative forms. Specific embodiments of the present invention are shown by way of example in the drawings and are described herein in detail. It should be understood, however, that the description set forth herein of specific embodiments is not intended to limit the present invention to the particular forms disclosed. Rather, all modifications, alternatives, and equivalents falling within the spirit and scope of the invention as defined by the appended claims are intended to be covered.

DETAILED DESCRIPTION OF SPECIFIC EMBODIMENTS

The description below illustrates embodiments of the present invention. For the sake of clarity, not all features of an actual implementation of the present invention are described in this specification. It should be appreciated that in connection with developing any actual embodiment of the present invention many application-specific decisions must be made to achieve specific goals, which may vary from one application to another. Further, it should be appreciated that any such development effort might be complex and time-consuming, but would still be routine for those of ordinary skill in the art having the benefit of this disclosure.

For the sake of clarity and convenience, the various embodiments are described herein in the context of interventional cardiovascular applications generally involving acute or transient ischemia or post-ischemic tissues. However, the present invention may also be useful in other medical applications, such as cancer therapy (e.g., the delivery of oxygen-enriched fluids directly into poorly vascularized tumors during radiation or chemotherapy treatments), neurovascular applications (e.g., the treatment of stroke and cerebral trauma patients), lung support in trauma and lung disease patients, and wound care management.

Also, although the present invention may be used to raise oxygen levels, for example, in venous and arterial blood, in blood substitutes, e.g., perfluorocarbons, and in combinations thereof, for the sake of clarity and convenience reference is made herein only to arterial blood.

Further, the present invention also may be used in connection with drug fluid infusion therapies to prevent ischemia and/or to otherwise enhance the effectiveness of the therapies. Examples of drug fluids used in cardiovascular and neurological procedures which may be infused (either before, after or along with the oxygenated blood) in accordance with the present invention include, without limitation, vasodilators (e.g., nitroglycerin and nitroprusside), platelet-actives (e.g., ReoPro and Orbofiban), thrombolytics (e.g., t-PA, streptokinase, and urokinase), antiarrhythmics (e.g., lidocaine, procainamide), beta blockers (e.g., esmolol, inderal), calcium channel blockers (e.g., diltiazem, verapamil), magnesium, inotropic agents (e.g., epinephrine, dopamine), perofluorocarbons (e.g., fluosol), crystalloids (e.g., normal saline, lactated ringers), colloids (albumin, hespan), blood products (packed red blood cells, platelets, whole blood), Na+/H+ exchange inhibitors, free radical scavengers, diuretics (e.g., mannitol), antiseizure drugs (e.g., phenobarbital, valium), and neuroprotectants (e.g., lubeluzole). The drug fluids may be infused either alone or in combination depending upon the circumstances involved in a particular application, and further may be infused with agents other than those specifically listed, such as with adenosine (Adenocard, Adenoscan, Fujisawa), to reduce infarct size or to effect a desired physiologic response.

Turning now to the drawings, a system is provided in which blood is oxygenated, e.g., for delivery to a particular predetermined area within a patient's body for the treatment of conditions such as tissue ischemia and post-ischemic tissues. As shown schematically in FIG. 1, one embodiment of such a system includes a blood pump assembly 20 adapted for receiving a supply of blood from a blood supply assembly 10. The blood supply assembly 10 may comprise a supply of blood provided for infusion to a patient or to another particular desired location. By way of example, and without limitation, the supply of blood may be received from a bag or other blood container; from a blood transferring device, such as a heart bypass system, blood oxygenator, blood filtration assembly, artificial heart and the like; from another individual; or from the patient.

The pump assembly 20 provides the blood to a blood oxygenation assembly 30. The oxygenation assembly 30 comprises an apparatus for raising the $pO_2$ of the blood, advantageously to hyperoxemic or hyperbaric levels. In one embodiment, the oxygenation assembly comprises a high pressure membrane oxygenator. In another embodiment, the oxygenation assembly comprises a liquid-to-liquid oxygenator.

The oxygenation assembly 30 oxygenates blood received from the pump assembly 20. The oxygenated blood is then provided to a delivery assembly 40 for delivery to a desired location. Advantageously, blood oxygenation occurs at least in part at a pressure greater than atmospheric pressure, and the oxygenated blood is delivered with a concomitant pressure drop, so that the formation of clinically significant bubbles is avoided, i.e., blood oxygenation and delivery occurs bubble-free.

What constitutes bubble-free delivery will vary depending upon the circumstances involved in a particular application. Advantageously, bubble-free delivery will occur with a complete absence of bubbles. However, in some cases of "bubble-free" delivery, one or more (perhaps maybe even thousands of) non-clinically-significant bubbles may be delivered, particularly where the gas bubbles comprise oxygen gas bubbles, which are thought to be more readily accepted by the body than bubbles of other gases. Moreover, a clinically acceptable level of bubbles in one application (e.g., a coronary procedure) might not prove to be clinically acceptable in another application (e.g., a neurological procedure).

Little hard data are available. However, for interventional cardiology applications, for example, one factor addressing the question of what constitutes a clinically significant bubble may be the total volume of gas, per kilogram body weight, delivered into the coronary circulation. In cases where the gas is air (as opposed to cases involving oxygen gas bubbles), experienced angiographers have witnessed a single bubble or multiple bubbles up to approximately 3 mm (3000 μm) in diameter, embolize into a coronary artery of a patient during an angiographic procedure without a resulting clinical problem. The volume of air in a 3 mm diameter bubble is approximately 14 microliters. Thus, this volume of air, embolized as a single bubble into a human coronary artery is benign. Moreover, Khan et al. (1995) Coronary Air Embolism: Incidence, Severity, and Suggested Approaches to Treatment, *Catheterization and Cardiovascular Diagnosis* 36:313–18, retrospectively studied 3715 coronary angiograms to assess the incidence and severity of coronary air embolism, and related clinical severity to bubble volume as follows: minimal (several bubbles that disappear immediately without symptoms); mild (1 ml air with mild, transient symptoms); moderate (2–3 ml air usually associated with severe symptoms); and massive (>3–5 ml air associated with serious, life threatening complications). The mild clinical effect observed with 1 ml of air in the study is about equivalent to experiencing a single bubble with a 12 mm diameter, since the volume of this bubble is 1 ml. Thus, it appears that a 3 mm diameter air bubble is clinically insignificant—it is a minimal volume of air per unit body weight.

Accordingly, for a coronary application in which the primary bubbles of interest are oxygen bubbles, it is believed that a total delivered gas volume of less than between about 1–2 ml represents clinical insignificance. However, because oxygen is metabolically consumed, oxygen bubble infusion is not thought to be as traumatic as the infusion of inert gases (e.g., nitrogen).

Turning now to FIG. 2, an exemplary oxygenation assembly is depicted schematically including a high pressure membrane oxygenator assembly 50. The membrane oxygenator assembly 50 includes a membrane 52 in effect dividing the assembly 50 into two separate fluid compartments: a gas side compartment 54 and a blood side compartment 56. Oxygen gas from an oxygen gas supply assembly 58 is provided to the interior of the compartment 54 at a pressure P1. Advantageously, the assembly 58 is a regulated oxygen bottle and the pressure P1 is a pressure greater than atmospheric and less than about 30 p.s.i.a. Most advantageously, the pressure P1 is about 2 atmospheres. Blood to be oxygenated is provided by a blood supply assembly 60 to the interior of compartment 56 at a pressure P2. Advantageously, the pressure P2 is greater than about P1, and bulk gas flow across the membrane 52 is avoided.

As the oxygen gas is provided to the compartment 54 and the blood provided by the blood supply assembly 60 flows through the compartment 56, oxygen diffuses across the membrane 52 to oxygenate the blood. Oxygenated blood exits the compartment 56 via a line 62, e.g., for delivery via a catheter to a patient's body.

In an alternate embodiment the membrane oxygenator assembly is adapted with a bulk gas exit vent 64, so that gas may flow through the compartment 54 when the vent 64 is open. Advantageously, the vent 64 includes an adjustable valve or other means operable to control the rate of gas flow through compartment 54 for a given pressure P1. The fluid stream exiting compartment 54 may be vented to the atmosphere or to suitable means for processing and disposing of the exiting fluid. Depending upon the circumstances involved in a particular application, gases may diffuse across the membrane 52 from the blood flowing through the compartment 56 to join the stream exiting compartment 54.

The form which the membrane oxygenator assembly 50 may take, and its exact size and shape, may vary depending upon the circumstances involved in a particular application.

By way of example only, and without limitation as to the scope of the present invention, the membrane oxygenator assembly 50 may comprise an external flow fiber bundle oxygenator in which the compartment 54 comprises a plurality of hollow fibers through which gas may flow; the compartment 56 comprises a housing or vessel surrounding the hollow fibers and within which blood provided to the interior of the housing or vessel may contact the outer surface of the hollow fibers; and the membrane 52 comprises the total active surface area of the hollow fibers across which oxygen diffuses when blood is provided to the interior of the housing or vessel and oxygen gas is provided to the interior of the hollow fibers.

In an alternate embodiment (see FIG. 3), the high pressure membrane oxygenator comprises an internal flow hollow-fiber type blood oxygenator assembly. Advantageously, the assembly includes a generally cylindrically shaped housing assembly loosely packed with a plurality of hollow fibers 70. The housing advantageously comprises a generally tubular main body portion 72 having first and second ends; and end caps 74, 76 fixedly attached (e.g., with UV adhesive) to the first and second ends, respectively. The ends of the hollow fibers 70 advantageously are secured within the housing assembly by a potting material, e.g., a polyurethane resin. Advantageously, the potting material forms fluid barriers 78, 80 proximate the first and second ends, respectively. The hollow fibers 70 extend through the barriers 78, 80, so that the housing assembly comprises four fluid flow regions within the housing assembly: a blood inlet manifold 82, comprising the fluid space defined by the barrier 78 and cap 74; a blood outlet manifold 84, comprising the fluid space defined by the barrier 80 and the cap 76; an oxygen chamber 86, comprising the fluid space defined by the barriers 78, 80, the housing body portion 72, and the external surfaces of the hollow fibers 70; and the interior of hollow fibers 70, which region comprises a plurality of continuous fluid pathways between the blood inlet and outlet manifolds 82, 84.

Advantageously, the end cap 74 includes a blood inlet port 88, and the cap 74 is adapted with a luer connector 92 for releasably coupling the oxygenator assembly to an apparatus for providing a supply of blood to be oxygenated. The end cap 76 includes a blood exit port 90, and the cap 76 is adapted with a luer connector 94 for releasably coupling the oxygenator assembly to an oxygenated blood delivery apparatus, e.g., a tube and catheter or infusion guidewire. The housing body portion 72 includes gas inlet and outlet ports 96, 98, respectively. The gas inlet port 96 advantageously is adapted with a luer connector 100 for releasably coupling the oxygenator assembly to an oxygen gas supply assembly. The gas outlet port 98 advantageously is adapted with a luer connector 102 for releasably coupling the oxygenator assembly to an apparatus for venting the stream of gas exiting the oxygenator assembly to the atmosphere or to a filter assembly prior to disposal.

Thus, a method is provided in which oxygen is supplied to the oxygen chamber 86 at a pressure above atmospheric. Blood enters the blood inlet manifold 82 via port 88 and travels through the hollow fibers 70 where oxygenation of the blood occurs by virtue of oxygen diffusion across the fibers 70. Bulk gas transfer is avoided by maintaining the blood pressure greater than the gas pressure. The oxygenated blood then exits the oxygenator assembly via blood outlet manifold 84 and port 90 for delivery to a given location.

The hollow fibers 70 advantageously comprise a 160 cm length of matted fibers (each fiber advantageously about 8–10 cm in length) loosely rolled into a cylindrical shape, so that about a 0.05 inch space remains between the outer diameter of the fiber roll and the inner diameter of the oxygenator housing. The ends of the fibers proximate the entrance and exit manifolds advantageously are open and clean. A particularly advantageous matted fiber commercially available for use is the Akzo Oxyphan™ fiber mat, a polyproplyene hollow fiber mat including 16.8 fibers/cm, each fiber having a wall thickness of about 50 $\mu$m and about a 280 $\mu$m inner diameter, available from Akzo Nobel, Germany.

For a given input blood $pO_2$ and a specified oxygen pressure on the gas side of the membrane, as well as a specified blood flow rate and fiber housing diameter, a membrane oxygenator length can be determined to ensure equilibrium oxygen saturation. Of course, many variations are possible. By way of example only, and without limitation, a unit having a diameter of about 4 cm and length of about 10 cm, with a void volume of about 0.4 for fibers of about 380 $\mu$m O.D. and about 280 $\mu$m I.D., is sufficient to achieve equilibrium saturation for a blood flow rate of about 200 ml/min. Such a device would have a total blood priming volume of about 41 ml. Of course lower blood flow rates, smaller diameter fibers, tighter fiber packing, and overdriving the oxygen pressure will reduce the size requirement of the device, which is independent of desired blood $pO_2$. In any event, the extensive characterization of mass transfer coefficients that is typically required for external blood flow membrane oxygenators is unnecessary, and smaller priming volumes may be achieved.

Figure 16:
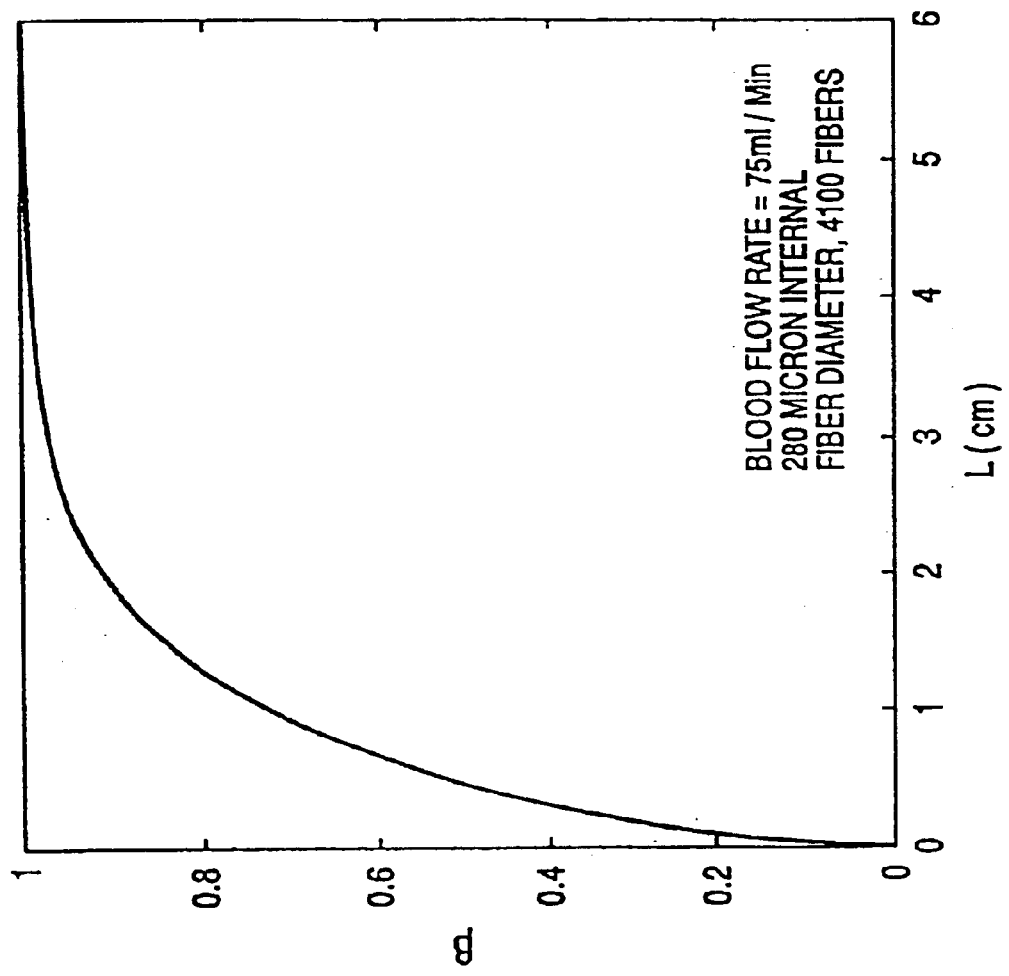
FIG. 16 is a graph, for exemplary embodiments of a high pressure membrane oxygenator, of oxygenator efficiency as a function of oxygenator length for an exemplary blood flow rate, in accordance with the present invention.

In one embodiment, oxygen transfer to the blood may be approximated using a model based on the convective-diffusion equation which considers blood flow through a circular tube as a variant of the Graetz-Nusselt-Leveque mass transfer problem for diffusion of solute through the walls of a tube in which the solvent experiences laminar Hagen-Poiseuille flow. Under this model, for oxygen supplied through the tube walls at a partial pressure equal to the pressure of oxygen gas supplied to the oxygenator, as shown by way of example in FIG. 16, oxygenator size may be determined through application into the model of several variables (e.g., blood flow rate, oxygen solubility, the number and/or size of the fibers, oxygen diffusivity in the blood, etc.). For a desired maximum blood flow rate $Q_{max}$, oxygenator size advantageously is minimized so that a desired efficiency $\beta$ may be achieved, where $\beta$ is the ratio of the outlet blood $pO_{2(out)}$ and the oxygen gas pressure. As shown in FIG. 16, for a blood flow rate of 75 ml/min with an oxygenator including 4100 fibers of 280 $\mu$m internal diameter, an oxygenator length of about 6 cm or more results in an efficiency $\beta=1$.

Other models for determining oxygen transfer also may be used, e.g., models based on empirical evidence of mass transfer coefficients, or mass transfer models tailored for specific applications involving other mass transfer boundary conditions, flow geometries, fluids, operating parameters, etc. Advantageously, the oxygen transfer model may be used to characterize an oxygenator to promote its selection by a caregiver for a particular application. In one embodiment, a method is provided including the steps of using an oxygen transfer model to characterize an oxygenator assembly to promote selection of the device for an application in which oxygenated blood is to be provided to the patient at a desired flow rate and $pO_2$. More advantageously, the oxygenated blood is provided at a $pO_2$ level greater than about 760 mm Hg.

Because the device advantageously may be designed for equilibrium mass transfer, equilibrium heat transfer may occur also. Thus, a system requirement may include means for controlling the temperature of the blood exiting the assembly. By way of example, a simple heating device might include, e.g., an electric blanket wrapped around the oxygenator unit, with feedback control, for maintaining the temperature of the blood at about 37 ° C.

Figure 4:
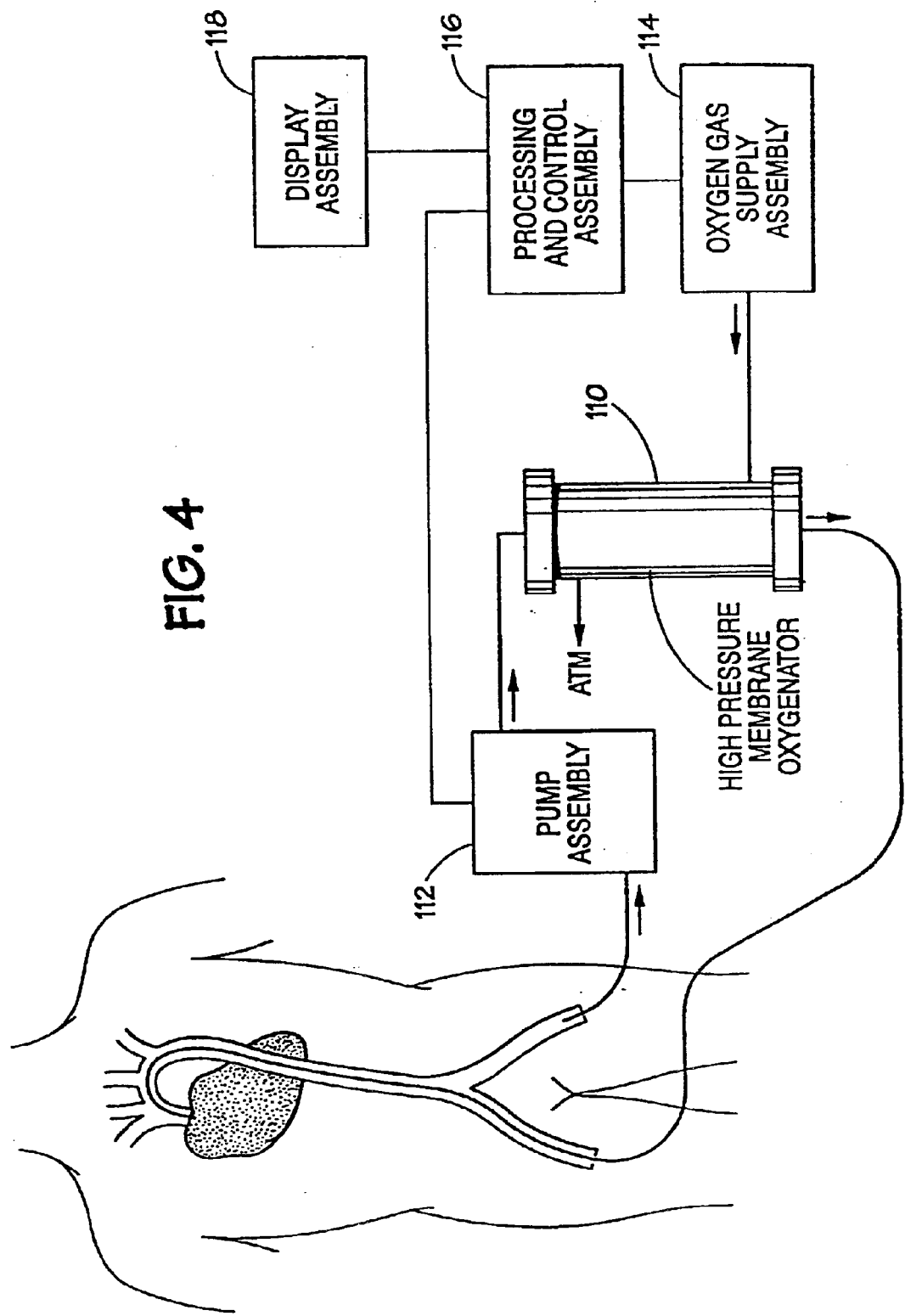
FIG. 4 is a schematic diagram illustrating an exemplary embodiment of an extracorporeal circuit including a blood oxygenation system having a high pressure membrane oxygenator in accordance with the present invention.

Turning to FIG. 4, an extracorporeal circuit for oxygenating blood including a high pressure membrane oxygenator 110 is shown. The system requirements may include a blood pump assembly 112 and an oxygen gas supply assembly 114 operatively coupled to the high pressure membrane oxygenator 110. Other components may include blood temperature control devices, bubble detection apparatus, pressure/temperature sensors, $pO_2$ sensors, etc. (not shown in FIG. 4). Advantageously, the various system components are operatively coupled to a processing and control assembly 116 including electronic circuitry to enable the sending and receiving of signal inputs and/or control commands amongst one or more of the various system components. A display assembly 118 coupled to the processing and control assembly 116 may serve as a separate user interface for the input of data and/or process control commands and/or for the display of system status and/or processing outputs.

The flow characteristics of the oxygenated blood exiting the membrane oxygenator assembly 110 will depend upon the circumstances surrounding the particular application involved. Typically, for example, the supply of oxygenated blood provided to a catheter for infusion to a patient's body will be a controlled flow defined by the flow parameters selected by the caregiver. In an application involving the sub-selective delivery of oxygenated blood for the treatment of ischemic tissues and/or the prevention of ischemia, flow rates of about 75–100 ml/min may be advantageous. Again, factors influencing the determination of blood flow characteristics may include one or more of the many clinical parameters or variables of the oxygenated blood to be supplied to the catheter or to be delivered to the patient, e.g., the size of the patient, the percentage of overall circulation to be provided, the size of the blood vessel to be accessed, hemolysis, hemodilution, $pO_2$, pulsatility, mass flow rate, volume flow rate, temperature, hemoglobin concentration and pH.

Turning to FIG. 5, shown schematically is an alternate embodiment of an oxygenation assembly including a liquid-to-liquid oxygenation assembly 200. The assembly 200 advantageously combines a supply of oxygen-supersaturated fluid received from a supply assembly 210 with a supply of blood received from a supply assembly 220 to form oxygenated blood for delivery to a given location.

In one embodiment, the oxygen-supersaturated fluid advantageously includes a dissolved oxygen volume normalized to standard temperature and pressure of between about 0.5 and about 3 times the volume of the solvent. The fluid may be supplied to the system at a pressure of between about 100 p.s.i. and about 5000 p.s.i., more advantageously between about 100 p.s.i. and 600 p.s.i., although the exact pressure may vary depending upon the circumstances involved in a particular application. Further, the oxygen-supersaturated fluid supplied may be sterile and have a delivery path which does not include gas or surface sites at which potentially clinically significant bubbles may nucleate and/or grow.

As described herein, one preferred fluid for use in accordance with the present invention is an oxygen-supersaturated fluid. However, other gas-supersaturated fluids may be used depending upon the circumstances involved in a particular desired application, such as, for example, supersaturated fluids in which one or more gases such as helium, nitrous oxide, carbon dioxide and air are dissolved.

Exemplary apparatus and methods for the preparation and delivery of oxygen-supersaturated fluids are disclosed in U.S. Pat. No. 5,407,426 to Spears entitled "Method and Apparatus for Delivering Oxygen into Blood"; U.S. Pat. No. 5,569,180 to Spears entitled "Method for Delivering a Gas-Supersaturated Fluid to a Gas-Depleted Site and Use Thereof"; U.S. Pat. No. 5,599,296 to Spears entitled "Apparatus and Method of Delivery of Gas-Supersaturated Liquids"; and U.S. Pat. No. 5,893,838 to Daoud et al. entitled "System and Method for High Pressure Delivery of Gas-Supersaturated Fluids"; each of which is incorporated herein by reference. Furthermore, disclosure relating to exemplary apparatus and methods for the preparation and/or use of gas-supersaturated fluids, including, e.g., oxygen-supersaturated fluids, in various applications, may be found in the following patents and patent applications, each of which is incorporated herein by reference: copending U.S. patent application Ser. No. 08/581,019, filed Jan. 3, 1996, which is a continuation in part of U.S. patent application Ser. No. 273,652, filed Jul. 12, 1994, now U.S. Pat. No. 5,569,180, which is a continuation in part of U.S. patent application Ser. No. 152,589, filed Nov. 15, 1993, now U.S. Pat. No. 5,407,426, which is a continuation in part of U.S. patent application Ser. No. 818,045, filed Jan. 8, 1992, now U.S. Pat. No. 5,261,875, which is a continuation of U.S. patent application Ser. No. 655,078, filed Feb. 14, 1991, now U.S. Pat. No. 5,086,620.

In an alternate embodiment (see FIG. 10), the oxygen-supersaturated fluid supply assembly comprises an apparatus including a chamber 300 coupled to a regulated source of oxygen gas 310 that maintains a desired pressure in the chamber 300. Advantageously, the chamber volume is about 100 ml, and the pressure in the chamber 300 is about 600 p.s.i. A physiologic fluid (e.g., saline) enters the chamber 300 through a nozzle 320. The nozzle 320 advantageously forms fluid droplets into which oxygen diffuses as the droplets travel within the chamber 300. More advantageously, the nozzle 320 comprises an atomizer nozzle adapted to form a droplet cone 330 definable by an included angle $\alpha$, which advantageously is about 20 to about 40 degrees at operating chamber pressures (e.g., about 600 p.s.i.) for a pressure drop across the nozzle 320 of greater than approximately 15 p.s.i. The nozzle 320 is a simplex-type, swirled pressurized atomizer nozzle including a fluid orifice of about 100 $\mu$m diameter. Advantageously, the nozzle 320 forms fine fluid droplets of less than about 100 $\mu$m diameter, and more advantageously of about 25 $\mu$m. The fluid advantageously is provided to the chamber 300 by a pump 340 operatively coupled to a fluid supply assembly 350. The fluid advantageously is provided at a controlled rate based on the desired oxygen-supersaturated fluid outlet flow rate. At the bottom of the chamber 300, fluid collects to form a pool 360 which advantageously includes fluid having a dissolved gas volume normalized to standard temperature and pressure of between about 0.5 and about 3 times the volume of the solvent. The fluid is removed from the chamber 300 (e.g., via a pump 370, which advantageously permits control of the flow rate, or by virtue of the pressure in the chamber 300) for delivery to a given location (e.g., to a blood oxygenation assembly).

Figure 11:
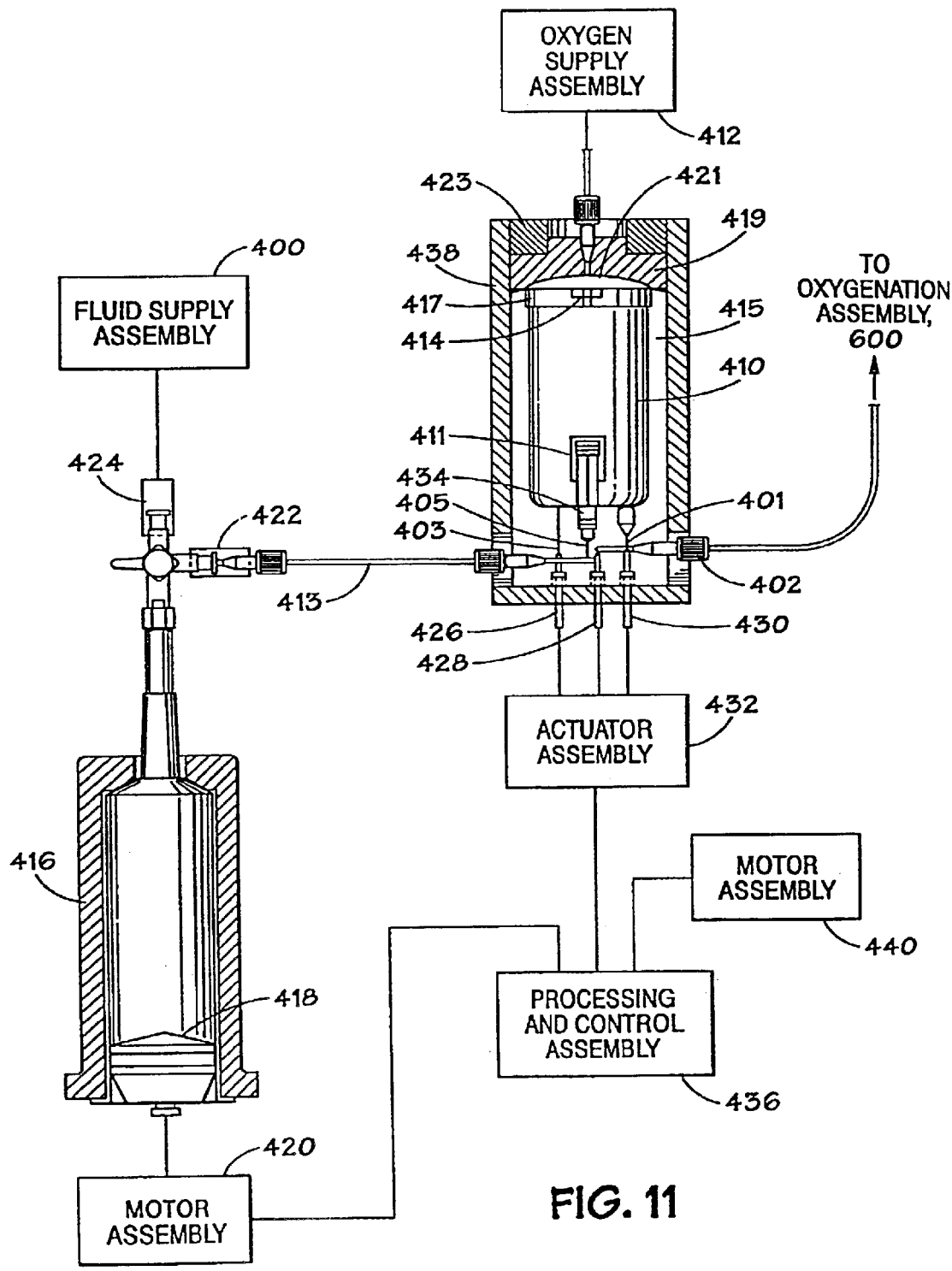
FIG. 11 is a schematic diagram illustrating an alternate exemplary embodiment of a system for supplying an oxygen-supersaturated fluid.

More advantageously, as shown in FIG. 11, oxygen-supersaturated fluid is produced by atomizing a physiologic liquid such as saline provided from a supply assembly 400 into a chamber 410 pressurized to about 600 p.s.i by oxygen. The oxygen advantageously is provided to the chamber 410 from an oxygen supply assembly 412, e.g., a medical grade E-bottle.

Saline advantageously is provided to the chamber 410 (e.g., from a saline bag or other container) via nozzle 411 by a piston-like assembly comprising an syringe pump 416 capable of delivering 600+ p.s.i. saline either continuously or intermittently depending upon the circumstances involved in a particular application. The syringe pump 416 advantageously includes a piston 418 operatively coupled to a motor assembly 420. A check valve 422 prevents unwanted loss of fluid from the line 413 during filling of the syringe pump 416. A check valve 424 prevents unwanted flow of saline to the fluid supply assembly 400 as fluid exits the syringe pump 416. Advantageously, the syringe pump 416 includes a fluid reservoir having a volume of about 10 to about 100 ml, although different size syringe pumps may be used depending upon the circumstances involved in a particular application. In addition, the chamber inlet advantageously is filtered to protect from any debris that might be present in the pumping system.

Three needle valves 426, 428, 430 advantageously are used to control the flow of fluid to and from the chamber 410. Table II describes the modes of operation for the needles. During normal operation, the pumping system is off and only the delivery valve (needle 430) is open to allow fluid delivery from the chamber 410 via fluid exit lumen 401 and the assembly outlet 402, e.g., to a blood oxygenation assembly. When the chamber needs to be filled (e.g., in response to a sensor signal indicating that the fluid level in the chamber has dropped to a predetermined level), a two-part filling sequence advantageously begins. In part one of the filling sequence, the pumping system is on and dilution flow is on, i.e., dilution valve (needle 426) is open to allow fluid delivery from the line 413 to the chamber 410 via line 403. In part two, needle 426 is closed, and flow is directed from line 413 through the atomizer nozzle 411 via line 405. The delivery valve (needle 430) remains open during both parts of the filling sequence. By varying the time of each part of the filling sequence, the concentration of the fluid in the chamber can be varied. For example, to achieve a 300 p.s.i. concentration in a chamber pressurized to 600 p.s.i., for a 40 second total fill time each part of the two-part filling sequence would last about 20 seconds. Check valve 434 prevents backflow from the chamber through the atomizer nozzle to the pumping system as the pumping system reservoir is being filled. Advantageously, check valve 434 includes a ball which seats under pressure against a portion of the valve body to prevent unwanted backward fluid flow. Further, to bypass the chamber, i.e., so that fluid neither enters nor exits the chamber, a flush sequence is initiated. During flush, the delivery valve (needle 430) and the dilution valve (needle 426) are closed, the flush valve (needle 428) is open, and the pumping system is on, so that unoxygenated saline passes through the system.

TABLE II

| | Pump State | Valve State | | |
| --- | --- | --- | --- | --- |
| | | Needle 426 | Needle 428 | Needle 430 |
| Normal Operation Filling Sequence | Off | Closed | Closed | Open |
| Part 1 | On | Open | Closed | Open |
| Part 2 | On | Closed | Closed | Open |
| Flush sequence | On | Closed | Open | Closed |

Advantageously, each of the needles 426, 428, 430 is opened and closed either independently or in conjunction with the opening or closing of one or more other needles, to achieve a desired flow of oxygen-supersaturated fluid from the assembly. The actuator assembly 432 may comprise switching means, e.g., solenoids, operatively coupled to each valve to move the valves between open and closed positions.

The chamber 410 advantageously comprises a disposable housing 415 and cap 417 joined (e.g., by threaded engagement) or fixedly attached (e.g., by UV adhesive) so as to define the interior space into which saline and oxygen are introduced. The chamber 410 further may include a bacterial filter assembly 414 for removing unwanted particulates from the gas entering the chamber 410. The housing 415 and cap 417 may be formed of polycarbonate or of another suitable biocompatible material.

For safety, the chamber 410 may be disposed at least in part within a protective housing assembly 438, comprising, e.g., a stainless steel holder. In one embodiment, a block 419 may be positioned within the holder 438 above the chamber 410. Advantageously, the block 419 is adapted with a recess or generally concave-shaped lower surface portion, so that a gas plenum 421 is defined by the lower surface of the block 419 and the upper end or surface of the chamber 410. Advantageously, the boundary between the block 419 and chamber 410 is sealed (e.g., with an o-ring, gasket or other sealing means). A ring 423 in threaded engagement with the holder 438 may help retain the block 419 sealed and in place against chamber 410 when oxygen gas from the supply assembly 412 is introduced into the plenum 421 through a gas inlet port in the block 419. From the plenum 421 gas may enter the chamber 410 through the filter 414 disposed along a port through the cap 417. Advantageously, gas pressure within the plenum 421 and the chamber 410 are about equal.

Advantageously, the chamber 410 and other system components include one or more sensors, e.g., fluid level sensors, pressure tranducers, etc., (not shown in FIG. 11) to enable the monitoring of system status during operation. Advantageously, the sensors and various system components are coupled to a processing and control assembly 436 including electronic circuitry to enable the sending and receiving of signal inputs and/or control commands amongst one or more of the various system components. A display assembly 440 coupled to the processing and control assembly 436 may serve as a separate user interface for the input of data and/or process control commands and/or for the display of system status and/or processing outputs.

Figure 10:
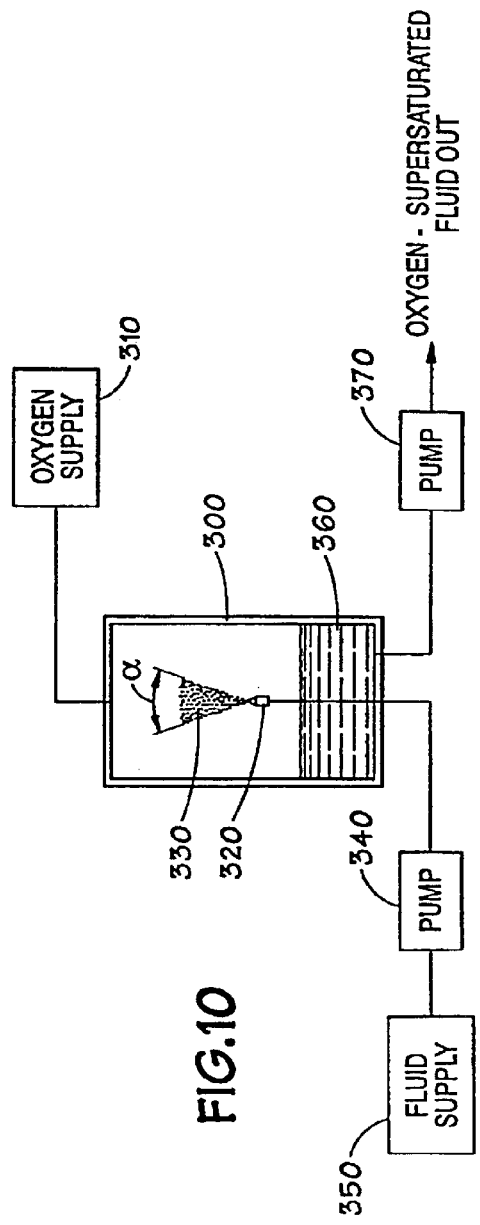
FIG. 10 is a schematic diagram illustrating an exemplary embodiment of a system for supplying an oxygen-supersaturated fluid.

For the sake of clarity and convenience, oxygen-supersaturated fluid supply assemblies such as the ones shown in FIGS. 10 and 11 have been described including liquid atomizing assemblies. However, other means for contacting the liquid and gas may be used. For example, in some cases it may be desirable to provide the liquid within the pressurized chamber as a thin film in contact with oxygen gas. The liquid film may be created, for example, by plates, sieves, screens or other mechanical means either disposed within or forming part of the chamber. Moreover, fluid supply assemblies other than the pump and syringe pump embodiments, valving arrangements, and/or liquid flow paths shown may be used in combination with the various other components described herein.

Turning now to FIG. 6, an extracorporeal blood oxygenation circuit is shown including a pump assembly 500 operable to deliver blood withdrawn from a patient to an exemplary liquid-to-liquid oxygenation assembly 600. The assembly 600, portions of which are shown in greater detail in FIGS. 7A–E, advantageously includes an injector housing 610, a sidewall assembly 620, and a cap 630 joined so as to define an interior space 612 within which blood provided by the supply tube 640 mixes with oxygen-supersaturated fluid provided by the capillary assembly 650 to form oxygenated blood. The oxygenated blood exits the interior space 612 via outlet 614 for delivery via return tube 660 to a fluid delivery apparatus 510. The injector housing 610, sidewall assembly 620, cap 630, and other assembly components advantageously are disposable and are made of biocompatible materials, e.g., polycarbonate, polyethelyene and the like. The tubing advantageously comprises medical grade PVC tubing.

The blood supply tube 640, which may include a pressure monitoring port 642, advantageously comprises a continuous blood flow path between a first tube end operatively coupled to the outlet of the blood pump assembly 500 and a second tube end fixedly attached to the injector housing 610 and in fluid communication with the interior space 612, e.g., via a fluid passageway 644 extending through at least a portion of the housing 610 and including a fluid port 646. Advantageously, blood exits through port 646 so as to create a vortical or cyclonic flow within the interior space 612, e.g., along a path substantially tangential to the chamber wall.

The capillary assembly 650 advantageously includes a single fused silica capillary having a 100 μm inner diameter and a 350 μm outer diameter, which comprises a continuous fluid pathway between a first end of the assembly 650 operatively coupled to the outlet of an oxygen-supersaturated fluid supply assembly 550 and a second end of the assembly 650 disposed to allow fluid exiting the capillary to enter the interior space 612 of the liquid-to-liquid oxygenator. Advantageously, the capillary assembly 650 includes between its first and second ends a luer fitting 652 for securing the capillary in place upon being positioned within a lumen 654 passing through at least a portion of the injector housing 610 to the interior space 612. The capillary assembly advantageously may further include a support assembly (e.g., a rigid tube within which at least a portion of the capillary is disposed) proximate the second end of the assembly 650 to help maintain the capillary fluid outlet port in place within the interior space 612, and/or a strain relief assembly (e.g., a flexible tube within which at least a portion of the capillary is disposed) to help prevent excessive bending or kinking of the capillary.

Alternately, the capillary assembly 650 may comprise a plurality of capillaries having inner diameters in the range of about 20 μm to about 1000 μm, with an inner diameter of about 100 μm to about 125 μm being particularly advantageous. The capillaries advantageously are potted together or otherwise joined at their outer surfaces to form a single capillary bundle. The capillaries also may be formed of glass, PEEK (poly ether ether ketone) or other biocompatible material. Treating the capillaries with a water-wettable coating or liquid rinse prior to use may prove advantageous to help ensure that the capillary inner surface(s) do not promote clinically significant bubble formation.

Advantageously, the interior space 612 is pressurizable, so that during operation a supply of blood accumulates in the bottom and a gas head remains in the top of the liquid-to-liquid oxygenation assembly. The cap 630 may be adapted with a port 632 to allowing monitoring of the pressure within the interior space 612. The assembly also may include one or more fluid sample ports, e.g., port 634 on return tube 660.

The flow characteristics of the oxygenated blood exiting the liquid-to-liquid oxygenation assembly 600 will depend upon the circumstances surrounding the particular application involved. Typically, for example, the supply of oxygenated blood provided to a catheter for infusion to a patient's body will be a controlled flow defined by the flow parameters selected by the caregiver. In an application involving the sub-selective delivery of oxygenated blood for the treatment of ischemic myocardial tissues and/or the prevention of myocardial ischemia, flow rates of about 75–100 ml/min may be advantageous. Again, factors influencing the determination of blood flow characteristics may include one or more of the many clinical parameters or variables of the oxygenated blood to be supplied to the catheter or to be delivered to the patient, e.g., the size of the patient, the percentage of overall circulation to be provided, hemolysis, hemodilution, $pO_2$, pulsatility, mass flow rate, volume flow rate, temperature, target blood vessel, hemoglobin concentration and pH.

It is possible to approximate the $pO_2$ of the oxygenated blood exiting the liquid-to-liquid oxygenation assembly 600 for a particular application. Advantageously, the processing and control assembly includes a computer, electronic circuitry, and/or processing software embedded within electronic circuitry (e.g., programmed electronic chips) that continuously executes a $pO_2$ approximation model during system operation that accounts and corrects as necessary for possible $pO_2$ variations resulting from variables such as temperature, pH, Base excess (BE), $pCO_2$, $P_{50}$, hemoglobin-oxygen saturation levels, etc. The processing and control assembly advantageously displays model results (e.g., predicted $pO_2$) for the caregiver on the display assembly along with one or more of the input, sensed, calculated or otherwise obtained values of the variables related to the model.

For example, one $pO_2$ approximation model advantageously may be based on the Severinghaus equation. See Severinghaus, J. W., Simple, Accurate Equations for Human Blood $O_2$ Dissociation Computations, *Journal of Applied Physiology* 46(3):599–602. Advantageously, the oxygenated fluid $pO_2$ and oxygen concentration values are adjusted to correct for any difference between the temperature of the oxygenated fluid entering the liquid-to-liquid oxygenation assembly and the temperature of the oxygenated blood to be infused. The hemoglobin-oxygen saturation is calculated to estimate the quantity, if any, of oxygen from the oxygenated fluid that will bind to hemoglobin before effecting an increase in plasma oxygen levels. The difference between the initial oxygen content of the patient's blood and the calculated oxygen content that would achieve 100% hemoglobin saturation represents the amount of oxygen that will be bound by the hemoglobin before plasma $pO_2$ elevation. By calculating the concentration of the oxygenated fluid delivered into the flowing blood, and then adjusting that amount downward by an amount equal to the amount of oxygen that will be bound by the hemoglobin before plasma $pO_2$ elevation, the predicted $pO_2$ can be obtained by combining the adjusted oxygenated fluid concentration with the initial patient $pO_2$.

Figure 14:
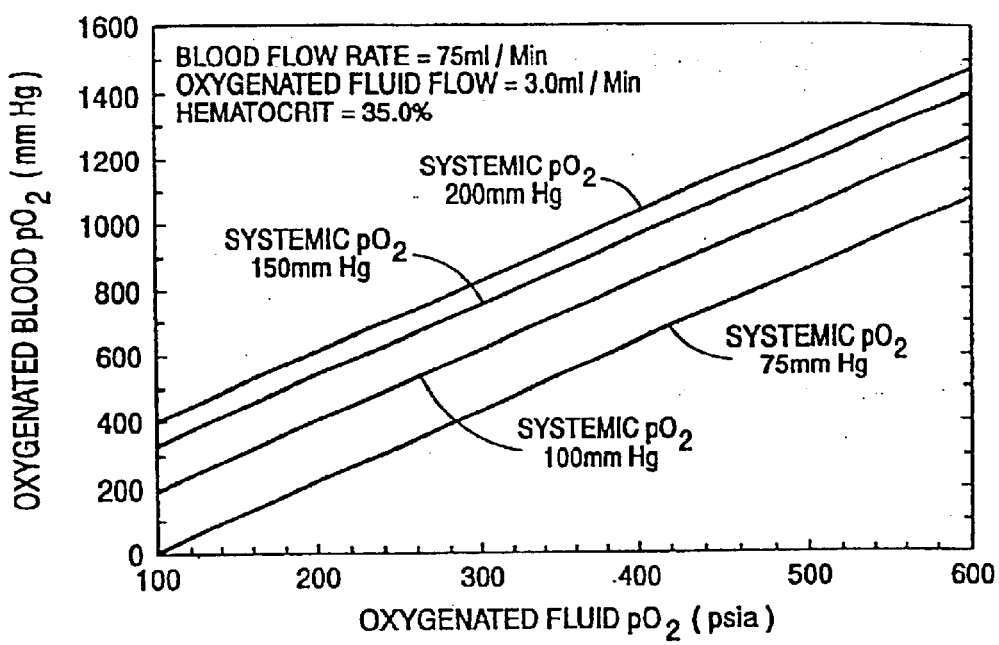
FIG. 14 is a graph, for an exemplary oxygenated blood fluid delivery apparatus, of predicted oxygenated blood $pO_2$ as a function of oxygenated fluid $pO_2$ and patient systemic $pO_2$, in accordance with the present invention.
Figure 15:
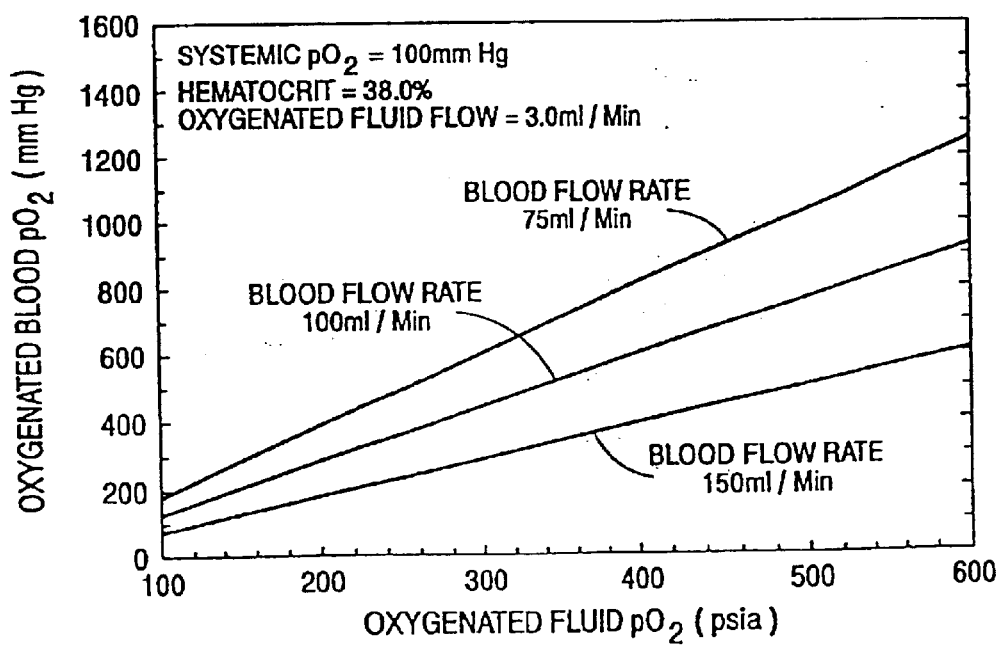
FIG. 15 is a graph, for an exemplary oxygenated blood fluid delivery apparatus, of predicted oxygenated blood $pO_2$ as a function of oxygenated fluid $pO_2$ and blood flow rate, in accordance with the present invention.

Exemplary predicted $pO_2$ values obtained using an approximation model based on the Severinghaus equation are set forth in FIGS. 14 and 15. FIG. 14 shows predicted $pO_2$ as a function of oxygenated fluid $pO_2$ and patient systemic $pO_2$. FIG. 15 shows predicted $pO_2$ as a function of oxygenated fluid $pO_2$ and blood flow rate. Depending upon the circumstances involved in a particular application, other $pO_2$ approximation models advantageously may be used. Such other approximation models may be based, for example, on other equations and/or methods for determining $pO_2$, such as those described in Sharan, M., Singh, M. P., Aminataei, A. (1989) A Mathematical Model for the Computation of the Oxygen Dissociation Curve in Human Blood, *Biosystems* 22(3):249–60; and Siggard-Anderson, O., Wimberley, P. D., Gothgen, I., Siggard-Anderson, M. (1984) A Mathematical Model of the Hemoglobin-Oxygen Dissociation Curve of Human Blood and of Oxygen Partial Pressure as a Function of Temperature, *Clin. Chem.* 30(10):1646–51.

The delivery apparatus 510 may comprise any clinically acceptable fluid delivery device such as a catheter (e.g., rapid exchange, over-the-wire, etc.), infusion guidewire, sheath and the like. By way of example only, as shown in FIGS. 8 and 8A–F, one such delivery device comprises a catheter 700 including a proximal end 710 adapted for coupling to the outlet of an oxygenation assembly (see, e.g., the assemblies shown in FIGS. 4 and 6) and a distal end 720 removably insertable within a patient's body. Advantageously, the catheter 700 includes a relatively stiff proximal portion 730, to provide pushability and torqueability, a relatively flexible distal portion 740, that provides a balance of stiffness and flexibility to track the vasculature, and a transition portion 750 of intermediate relative stiffness and flexibility. The catheter 700 comprises a generally tubular member having a central lumen 760 forming a continuous fluid pathway between the ends 710, 720. The distal end 720 of the tubular member may be either open or closed. The distal portion 740 of the catheter 700 advantageously includes a second lumen 780 through at least a portion of its length. The second lumen 780 advantageously comprises a guidewire lumen of about 0.017 inch inner diameter and of sufficient length to promote tracking of the catheter over a 0.014 inch guidewire inserted through the lumen 780, and to allow rapid exchange of the catheter without the use of extension wires. A lumen 780 length of approximately 4 cm, a distal portion 740 length of about 5 cm, and an overall catheter length of about 140 cm may be advantageous, particularly for applications involving the sub-selective delivery of oxygenated blood.

Fluid advantageously may exit the central lumen 760 through an end hole located at the distal tip of the catheter 700 and/or through one or more sideholes 790 disposed along the distal portion 740. Advantageously, the sideholes 790 are located along the portion of the catheter extending back about 0.5 inches from the distal tip, with sequential sideholes advantageously spaced so that the sidehole throughway axes are generally perpendicular to the central axis of the catheter and about parallel to skewed axes circumferentially offset from each other by about 90 degrees (compare, e.g., FIGS. 8D and 8E). The fluid lumen may be of any shape, e.g., D-shaped, kidney-shaped, round, oval, square, etc.

The catheter 700 may include one or more radiopaque marker bands 800 to aid the caregiver in placement of the device. The catheter distal end 720 also may include an atraumatic tip, advantageously of 80 shore A hardness, to promote ease of placement without promoting clinically significant damage to vascular tissues. The proximal shaft advantageously has a higher shore hardness than the distal shaft to provide pushability. By way of example, the proximal portion 730 of the catheter may include a 5 Fr outer diameter, a 3.6 Fr inner diameter and be made of a 70 shore D material; and the distal portion 740 may include a 3.8 Fr outer diameter, a 2.3 Fr inner diameter fluid lumen 760 and be made of a 55 shore D material. Materials used to make the catheter 700 may include polyethylene or any other suitable biocompatible material (e.g., polyurethane, polyamide, polyester, elastomers, PET, thermoplastics, etc.).

Figure 9:
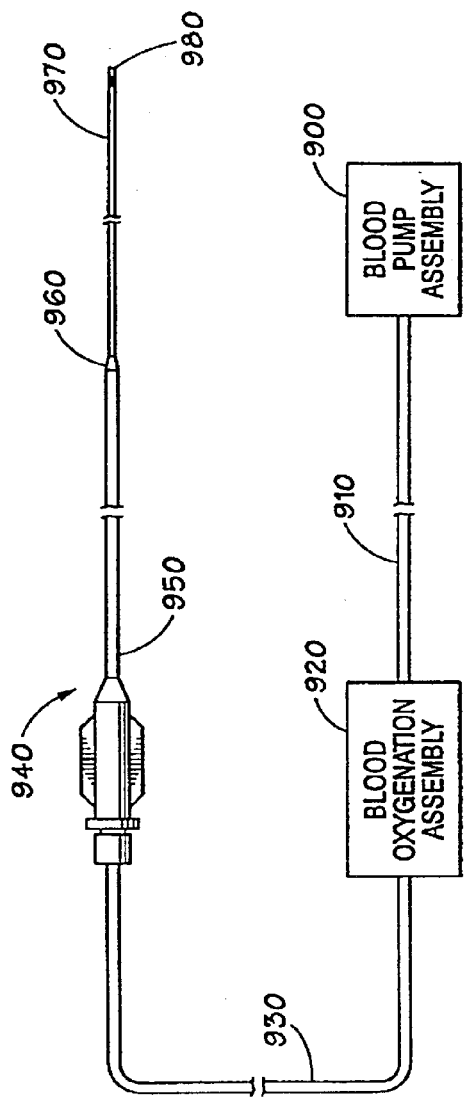
FIG. 9 is a schematic diagram illustrating an exemplary embodiment of an oxygenated blood fluid delivery apparatus in accordance with the present invention.

Turning to FIG. 9, an oxygenated fluid delivery apparatus advantageously includes a blood pump assembly 900; a first length of tubing 910 between the pump assembly 900 and a blood oxygenation assembly 920; a second length of tubing 930 between the blood oxygenation assembly 920 and a delivery assembly 940; and the delivery assembly 940. As shown in FIG. 9, the delivery assembly 940 includes a proximal portion 950, an intermediate portion 960, and a distal portion 970. Advantageously, the fluid delivery apparatus comprises a continuous fluid pathway between the blood pump assembly 900 and the distal tip 980 of the delivery assembly 940.

As shown in FIG. 9, the intermediate portion 960 may comprise a relatively short segment (e.g., about 1 cm in length) which necks down the proximal portion 950 to meet the distal portion 970. In alternate embodiments, the intermediate portion may comprise a transition segment of greater length including one or more portions joined end-to-end, each portion including an inner fluid lumen through which oxygenated blood may flow. By varying the size, shape and materials of the various catheter portions and oxygenated blood fluid lumens, a catheter having a desired effective diameter, handling characteristics, etc. may be provided for a particular desired application. Moreover, by varying the size and length of the tube 930, and/or including flow restrictors and/or other assemblies that affect the pressure drop along the oxygenated blood delivery pathway (e.g., a pressure cuff), a fluid delivery apparatus (which in some cases may be characterized in terms of an overall oxygenated blood fluid pathway effective diameter) may be provided for achieving a desired range of oxygenated blood $pO_2$ for a particular application.

Figure 12:
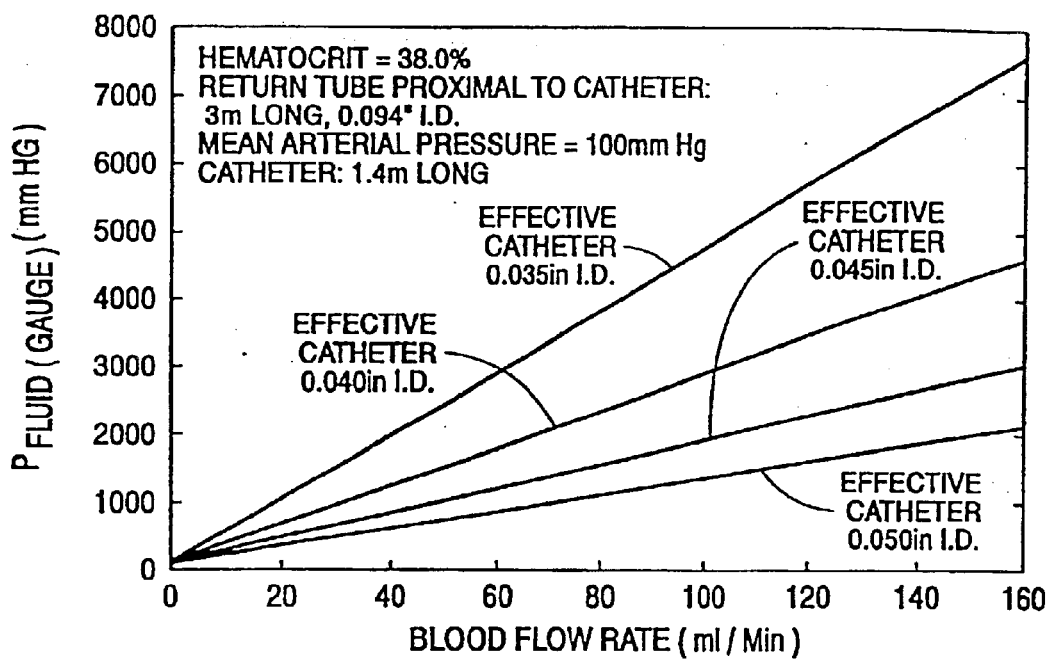
FIG. 12 is a graph, for an exemplary oxygenated blood fluid delivery apparatus, of oxygenated blood pressure at the oxygenation assembly as a function of blood flow rate and effective catheter inner diameter, in accordance with the present invention.
Figure 13:
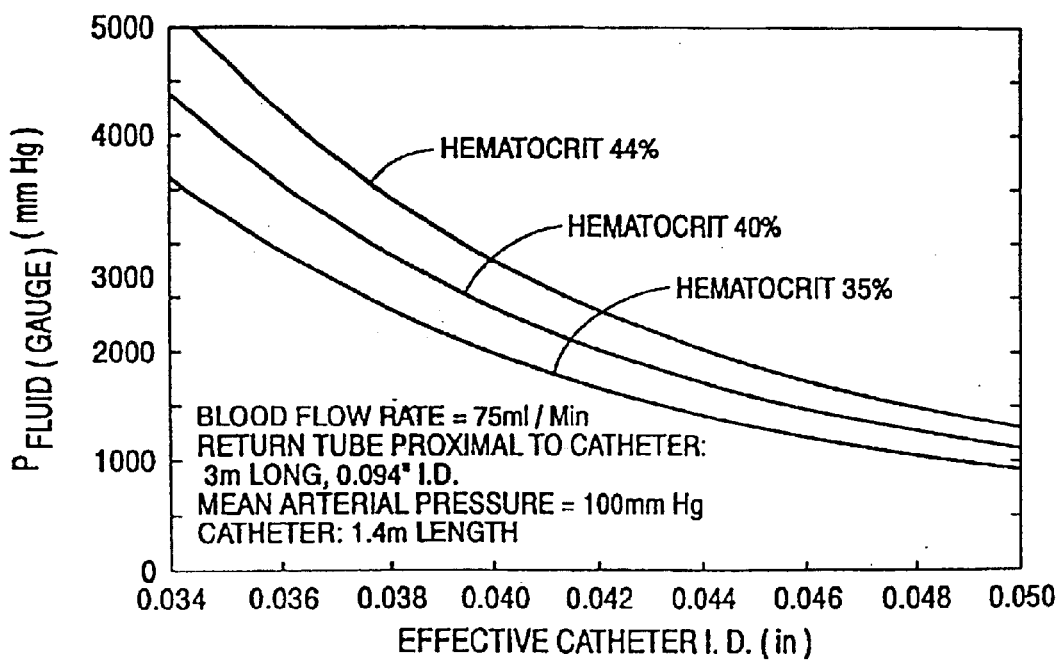
FIG. 13 is a graph, for an exemplary oxygenated blood fluid delivery apparatus, of oxygenated blood pressure at the oxygenation assembly as a function of effective catheter inner diameter and hematocrit, in accordance with the present invention.

By way of example, for an exemplary oxygenated blood fluid delivery apparatus comprising a 1.4 m long catheter coupled at its proximal end to a 3 m oxygenated blood return tube having a 0.094 inch inner diameter, oxygenated blood pressure at the oxygenation assembly 920 is plotted in FIG. 12 as a function of blood flow rate and catheter effective diameter for an exemplary application involving the delivery of oxygenated blood to a patient having a mean arterial pressure of 100 mm Hg and a 38% hematocrit, and plotted in FIG. 13 as a function effective catheter inner diameter and hematocrit for an exemplary application involving the delivery of oxygenated blood at 75 ml/min to a patient having a mean arterial pressure of 100 mm Hg. As shown in FIGS. 12 and 13, for a constant blood flow rate $Q_{blood}$, as the effective inner diameter of the catheter increases, the blood pressure $P_{fluid(gauge)}$ at the oxygenation assembly 920 decreases.

By knowing the simplified and approximated bubble-free delivery relationship, $\Delta P_{fluid} > pO_{2(out)}$, a caregiver having a catheter characterized by effective inner diameter can use a chart such as FIG. 12 to determine whether an appropriate range of blood flow rates are achievable if the caregiver were to use a fluid delivery apparatus including the catheter to deliver blood having a desired $pO_2$. Alternatively, a caregiver specifying a desired oxygenated blood $pO_2$ and oxygenated blood flow rate range can use a chart like the one shown in FIG. 12 as an aid to selecting a catheter for use in a fluid delivery apparatus for a particular application. Similarly, other such charts (e.g., FIG. 13) may be used by the caregiver or others in other applications for assistance in providing an oxygenated blood fluid delivery apparatus.

The present invention has been described in terms of exemplary embodiments. In accordance with the present invention, the operating parameters for the system may be varied, typically with a physician or caregiver specifying and selecting them for the desired clinical indication. Further, it is contemplated that other embodiments, which may be devised readily by persons of ordinary skill in the art based on the teachings set forth herein, may be within the scope of the invention which is defined by the appended claims. The present invention may be modified and practiced in different but equivalent manners that will be apparent to those skilled in the art having the benefit of the teachings set forth herein.

No limitations are intended to the details or construction or design shown herein, other than as described in the claims appended hereto. Thus, it should be clear that the specific embodiments disclosed above may be altered and modified, and that all such variations and modifications are within the spirit and scope of the present invention as set forth in the claims appended hereto.

What is claimed is:

1. A device for oxygenating blood and delivering the oxygenated blood to a patient, the device comprising:
    a blood pump assembly coupled to a supply of blood;
    a blood oxygenation assembly coupled to the blood pump assembly, the blood oxygenation assembly receiving the blood from the blood pump assembly and oxygenating the blood, the blood oxygenation assembly comprising:
        a mixing chamber having a first inlet, a second inlet, and an outlet;
        a pump adapted to deliver the blood to the mixing chamber via the first inlet,
        wherein the first inlet is positioned on the mixing chamber in such a way that the blood enters the mixing chamber substantially tangential to a wall of the mixing chamber; and
        a gas-supersaturated fluid supply assembly adapted to deliver an oxygen-supersaturated fluid having a liquid phase supersaturated with oxygen to the mixing chamber via the second inlet to mix with the blood and form the oxygenated blood, wherein the oxygenated blood exits the mixing chamber through the outlet; and
    a delivery system coupled to the blood oxygenation assembly, the delivery system being adapted to deliver the oxygenated blood to a patient, the delivery system comprising:
        a generally tubular elongated member having a proximal end portion and a distal end portion, the proximal end portion being adapted to be inserted into the patient and the distal end portion being coupled to the blood oxygenation assembly, the member further having a first lumen for carrying the oxygenated blood generally extending from the proximal end portion to the distal end portion, and the member having a transition portion located between the proximal end portion and the distal end portion, the transitional portion being relatively flexible compared to the proximal end portion and being relatively stiff compared to the distal end portion.

2. The device, as set forth in claim 1, comprising at least one hole located in a peripheral wall of the member and extending to the first lumen.

3. The device, as set forth in claim 2, wherein the at least one hole is formed in the distal end portion of the member.

4. The device, as set forth in claim 1, comprising a plurality of holes located in a peripheral wall of the member and extending to the first lumen.

5. The device, as set forth in claim 4, wherein the plurality of holes are formed in the distal end portion of the member.

6. The device, as set forth in claim 4, wherein each of the plurality of holes comprise a throughway axis, each throughway axis being generally perpendicular to a longitudinal axis of the member and being circumferentially offset from each adjacent throughway axis.

7. The device, as set forth in claim 1, comprising a second lumen extending along at least a portion of the member.

8. The device, as set forth in claim 7, wherein the second lumen is sized and located to promote tracking of the member over a guidewire.

9. The device, as set forth in claim 1, comprising a radiopaque marker located on the member.

10. A device for oxygenating blood and delivering the oxygenated blood to a patient, the device comprising:
    a blood pump assembly coupled to a supply of blood;
    a blood oxygenation assembly coupled to the blood pump assembly, the blood oxygenation assembly receiving the blood from the blood pump assembly and oxygenating the blood, the blood oxygenation assembly comprising:
        a mixing chamber having a first inlet, a second inlet, and an outlet;
        a pump adapted to deliver the blood to the mixing chamber via the first inlet,
        wherein the first inlet is positioned on the mixing chamber in such a way that the blood enters the mixing chamber substantially tangential to a wall of die mixing chamber; and
        a gas-supersaturated fluid supply assembly adapted to deliver an oxygen-supersaturated fluid having a liquid phase supersaturated with oxygen to the mixing chamber via the second inter to mix with the blood and form the oxygenated blood,
        wherein the oxygenated blood exits the mixing chamber through the outlet; and
    a delivery system coupled to the blood oxygenation assembly, the delivery system being adapted to deliver the oxygenated blood to a patient, the delivery system comprising:
        a generally tubular elongated member having a proximal end portion, a distal end portion, and a longitudinal axis, the proximal end portion being adapted to be inserted into the patient and the distal end portion being coupled to the blood oxygenation assembly, the member further having a first lumen extending from the proximal end portion to the distal end portion for carrying the oxygenated blood, and having a plurality of holes formed in a peripheral wall of the member and extending to the first lumen, the plurality of holes being located in the distal end portion of the member, each of the plurality of holes having a throughway axis, each throughway axis being generally perpendicular to the longitudinal axis of the member and being circumferentially offset from each adjacent throughway axis.

11. The device, as set forth in claim 10, comprising a second lumen extending along at least a portion of the member.

12. The device, as set forth in claim 11, wherein the second lumen is sized and located to promote tracking of the member over a guidewire.

13. The device, as set forth in claim 10, comprising a radiopaque marker located on the member.

14. The device, as set forth in claim 10, wherein each throughway axis is circumferentially offset from each adjacent throughway axis by 90 degrees.

15. The device, as set forth in claim 10, wherein the member comprises a transition portion located between the proximal end portion and the distal end portion, the transitional portion being relatively flexible compared to the proximal end portion and being relatively stiff compared to the distal end portion.

16. The device, as set forth in claim 10, wherein the plurality of holes are spaced at least 0.5 inches from a distal end of the member.

17. The device, as set forth in claim 10, wherein the plurality of holes are sequentially spaced along the longitudinal axis.

18. The device, as set forth in claim 10, wherein the first lumen terminates in an open distal end of the member.

19. The device, as set forth in claim 10, wherein the first lumen terminates in a closed distal end of the member.

20. A device for oxygenating blood and delivering the oxygenated blood to a patient, the device comprising:

a blood pump assembly coupled to a supply of blood;

a blood oxygenation assembly coupled to the blood pump assembly, the blood oxygenation assembly receiving the blood from the blood pump assembly and oxygenating the blood, the blood oxygenation assembly comprising:

a mixing chamber having a first inlet, a second inlet, and an outlet;

a pump adapted to deliver the blood to the mixing chamber via the first inlet, wherein the first inlet is positioned on the mixing chamber in such a way that the blood enters the mixing chamber substantially tangential to a wall of the mixing chamber; and a gas-supersaturated fluid supply assembly adapted to deliver an oxygen-supersaturated fluid having a liquid phase supersaturated with oxygen to the mixing chamber via the second inlet to mix with the blood and form the oxygenated blood, wherein the oxygenated blood exits the mixing chamber through the outlet; and a delivery system coupled to the blood oxygenation assembly, the delivery system being adapted to deliver the oxygenated blood to a patient, the delivery system comprising:

a generally tubular elongated member having a proximal end portion, a distal end portion, and a longitudinal axis, the proximal end portion being adapted to be inserted into the patient and the distal end portion being coupled to the blood oxygenation assembly, the member further having a first lumen extending from the proximal end portion to the distal end portion for carrying the oxygenated blood, and having a plurality of holes formed in a peripheral wall of the member and extending to the first lumen, the plurality of holes being located in the distal end portion of the member, each of the plurality of holes having a throughway axis, each throughway axis being generally perpendicular to the longitudinal axis of the member and being circumferentially offset from each adjacent throughway axis, the member further having a transition portion located between the proximal end portion and the distal end portion, the transitional portion being relatively flexible compared to the proximal end portion and being relatively stiff compared to the distal end portion.

21. The device of claim 1, 10, or 20, wherein the gas-supersaturated fluid supply assembly comprises a fluid supply;

a chamber having a first inlet, a second inlet, a third inlet and an outlet;

an oxygen gas supply coupled to deliver oxygen to the first inlet of the chamber;

a piston assembly coupled to receive fluid from the fluid supply and to deliver the fluid to the second inlet and the third inlet of the chamber;

a nozzle coupled to the third inlet of the chamber, the nozzle delivering the fluid from the piston assembly to the chamber;

a first valve coupled to the outlet of the chamber, the first valve being coupled to an actuator assembly to control delivery of oxygen-supersaturated fluid from the chamber, the outlet of the chamber being coupled to the second inlet of the blood oxygenation assembly to deliver the oxygen-supersaturated fluid into contact with the blood to form the oxygenated blood; and a second valve coupled to the second inlet, the second valve being coupled to an actuator assembly to control dilution during the creation of oxygen-supersaturated fluid within the chamber.

* * * * *